United States Patent
Marino et al.

(10) Patent No.: US 8,165,653 B2
(45) Date of Patent: *Apr. 24, 2012

(54) SURGICAL ACCESS AND NERVE SURVEILLANCE

(75) Inventors: James F. Marino, La Jolla, CA (US); Corbett W. Stone, San Diego, CA (US); Troy K. Christopher, San Diego, CA (US); Jeffrey J. Blewett, San Diego, CA (US); Brian S. Kelleher, Ramona, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/160,477

(22) Filed: Jun. 14, 2011

(65) Prior Publication Data

US 2011/0245843 A1 Oct. 6, 2011

Related U.S. Application Data

(60) Continuation of application No. 11/982,254, filed on Oct. 31, 2007, now Pat. No. 7,962,191, which is a continuation of application No. 11/489,020, filed on Jul. 18, 2006, which is a division of application No. 10/431,619, filed on May 7, 2003, now Pat. No. 7,079,883, which is a division of application No. 09/325,998, filed on Jun. 4, 1999, now Pat. No. 6,564,078.

(60) Provisional application No. 60/113,651, filed on Dec. 23, 1998, provisional application No. 60/120,663, filed on Feb. 19, 1999, provisional application No. 60/123,268, filed on Mar. 8, 1999.

(51) Int. Cl.
*A61B 5/04* (2006.01)
*A61B 17/08* (2006.01)
*A61M 29/00* (2006.01)

(52) U.S. Cl. .......................... 600/373; 606/198; 128/898
(58) Field of Classification Search .......... 600/373–374, 600/546–548, 554, 557; 128/898; 607/115–118; 606/32–52; 604/21–22, 27, 500, 912
See application file for complete search history.

(56) References Cited

U.S. PATENT DOCUMENTS

| 208,227 A | 9/1878 | Dorr |
|---|---|---|
| 972,983 A | 10/1910 | Arthur |

(Continued)

FOREIGN PATENT DOCUMENTS

DE 299 08 259 7/1999

(Continued)

OTHER PUBLICATIONS

Anatomy of the Lumbar Spine in MED TM MicroEndoscopic Discectomy (1997 Ludann Grand Rapids MI), 14 pgs.

(Continued)

*Primary Examiner* — Michael Peffley
*Assistant Examiner* — Ronald Hupczey, Jr.
(74) *Attorney, Agent, or Firm* — Jonathan Sprangler; Rory Schermerhorn

(57) ABSTRACT

An expandable tip cannula system, comprising: a hollow cannula shaft having a proximal end and a distal end; and an expandable tip mounted at the distal end of the hollow cannula shaft, the expandable tip comprising a plurality of generally-triangular shaped petals held together in a radially-inwardly tapered arrangement between adjacent petals, each petal comprising a nerve sensing electrode disposed therein.

12 Claims, 32 Drawing Sheets

U.S. PATENT DOCUMENTS

| | | | |
|---|---|---|---|
| 1,328,624 A | 1/1920 | Graham | |
| 1,548,184 A | 8/1925 | Cameron | |
| 2,704,064 A | 6/1955 | Fizzell et al. | |
| 2,736,002 A | 2/1956 | Oriel | |
| 2,808,826 A | 10/1957 | Reiner et al. | |
| 3,364,929 A | 1/1968 | Ide et al. | |
| 3,664,329 A | 5/1972 | Naylor | |
| 3,682,162 A | 8/1972 | Colyer | |
| 3,785,368 A | 1/1974 | McCarthy et al. | |
| 3,830,226 A | 8/1974 | Staub et al. | |
| 3,957,036 A | 5/1976 | Normann | |
| 4,099,519 A | 7/1978 | Warren | |
| 4,164,214 A | 8/1979 | Stark et al. | |
| 4,207,897 A | 6/1980 | Lloyd et al. | |
| 4,224,949 A | 9/1980 | Scott et al. | |
| 4,226,228 A | 10/1980 | Shin et al. | |
| 4,235,242 A | 11/1980 | Howson et al. | |
| 4,285,347 A | 8/1981 | Hess | |
| 4,291,705 A | 9/1981 | Severinghaus et al. | |
| 4,461,300 A | 7/1984 | Christensen | |
| 4,515,168 A | 5/1985 | Chester et al. | |
| 4,519,403 A | 5/1985 | Dickhudt | |
| 4,545,374 A * | 10/1985 | Jacobson | 600/210 |
| 4,561,445 A | 12/1985 | Berke et al. | |
| 4,562,832 A | 1/1986 | Wilder et al. | |
| 4,573,448 A | 3/1986 | Kambin | |
| 4,592,369 A | 6/1986 | Davis et al. | |
| 4,595,018 A | 6/1986 | Rantala | |
| 4,611,597 A | 9/1986 | Kraus | |
| 4,633,889 A | 1/1987 | Talalla | |
| 4,658,835 A | 4/1987 | Pohndorf | |
| 4,744,371 A | 5/1988 | Harris | |
| 4,759,377 A | 7/1988 | Dykstra | |
| 4,784,150 A | 11/1988 | Voorhies et al. | |
| 4,807,642 A | 2/1989 | Brown | |
| 4,892,105 A | 1/1990 | Prass | |
| 4,913,134 A | 4/1990 | Luque | |
| 4,926,865 A | 5/1990 | Oman | |
| 4,962,766 A | 10/1990 | Herzon | |
| 4,964,411 A | 10/1990 | Johnson et al. | |
| 5,007,902 A | 4/1991 | Witt | |
| 5,058,602 A | 10/1991 | Brody | |
| 5,081,990 A | 1/1992 | Deletis | |
| 5,092,344 A | 3/1992 | Lee | |
| 5,127,403 A | 7/1992 | Brownlee | |
| 5,161,533 A | 11/1992 | Prass et al. | |
| 5,171,279 A | 12/1992 | Mathews | |
| 5,195,541 A | 3/1993 | Obenchain | |
| 5,196,015 A | 3/1993 | Neubardt | |
| 5,255,691 A | 10/1993 | Otten | |
| 5,282,468 A | 2/1994 | Klepinski | |
| 5,284,153 A | 2/1994 | Raymond et al. | |
| 5,284,154 A | 2/1994 | Raymond et al. | |
| 5,299,563 A | 4/1994 | Seton | |
| 5,312,417 A * | 5/1994 | Wilk | 606/114 |
| 5,313,956 A | 5/1994 | Knutsson et al. | |
| 5,327,902 A | 7/1994 | Lemmen | |
| 5,333,618 A | 8/1994 | Lekhtman et al. | |
| 5,375,067 A | 12/1994 | Berchin | |
| 5,383,876 A | 1/1995 | Nardella | |
| 5,450,845 A | 9/1995 | Axelgaard | |
| 5,474,558 A | 12/1995 | Neubardt | |
| 5,480,440 A | 1/1996 | Kambin | |
| 5,482,038 A | 1/1996 | Ruff | |
| 5,484,437 A | 1/1996 | Michelson | |
| 5,509,893 A | 4/1996 | Pracas | |
| 5,540,235 A | 7/1996 | Wilson | |
| 5,560,372 A | 10/1996 | Cory | |
| 5,566,678 A | 10/1996 | Cadwell | |
| 5,571,149 A | 11/1996 | Liss et al. | |
| 5,579,781 A | 12/1996 | Cooke | |
| 5,593,429 A | 1/1997 | Ruff | |
| 5,599,279 A | 2/1997 | Slotman et al. | |
| 5,630,813 A | 5/1997 | Kieturakis | |
| 5,667,508 A | 9/1997 | Errico et al. | |
| 5,671,752 A | 9/1997 | Sinderby et al. | |
| 5,681,265 A | 10/1997 | Maeda et al. | |
| 5,707,359 A | 1/1998 | Bufalini | |
| 5,711,307 A | 1/1998 | Smits | |
| 5,728,046 A | 3/1998 | Mayer et al. | |
| 5,741,253 A | 4/1998 | Michelson | |
| 5,759,159 A | 6/1998 | Masreliez | |
| 5,772,661 A | 6/1998 | Michelson | |
| 5,775,331 A | 7/1998 | Raymond et al. | |
| 5,776,144 A | 7/1998 | Leysieffer et al. | |
| 5,779,642 A * | 7/1998 | Nightengale | 600/461 |
| 5,785,658 A | 7/1998 | Benaron | |
| 5,792,044 A | 8/1998 | Foley et al. | |
| 5,797,854 A | 8/1998 | Hedgecock | |
| 5,814,073 A | 9/1998 | Bonutti | |
| 5,830,151 A | 11/1998 | Hadzic et al. | |
| 5,851,191 A | 12/1998 | Gozani | |
| 5,853,373 A | 12/1998 | Griffith et al. | |
| 5,860,973 A | 1/1999 | Michelson | |
| 5,862,314 A | 1/1999 | Jeddeloh | |
| 5,872,314 A | 2/1999 | Clinton | |
| 5,885,219 A | 3/1999 | Nightengale | |
| 5,888,196 A | 3/1999 | Bonutti | |
| 5,902,231 A | 5/1999 | Foley et al. | |
| 5,928,139 A | 7/1999 | Koros et al. | |
| 5,928,158 A | 7/1999 | Aristides | |
| 5,935,131 A | 8/1999 | Bonutti et al. | |
| 5,938,688 A | 8/1999 | Schiff | |
| 5,944,658 A | 8/1999 | Koros et al. | |
| 5,976,094 A | 11/1999 | Gozani et al. | |
| 6,004,262 A | 12/1999 | Putz et al. | |
| 6,004,312 A | 12/1999 | Finnerman | |
| 6,027,456 A | 2/2000 | Feler et al. | |
| 6,038,469 A | 3/2000 | Karlsson et al. | |
| 6,038,477 A | 3/2000 | Kayyali | |
| 6,050,992 A | 4/2000 | Nichols | |
| 6,074,343 A | 6/2000 | Nathanson et al. | |
| 6,095,987 A | 8/2000 | Shmulewitz | |
| 6,104,957 A | 8/2000 | Alo et al. | |
| 6,104,960 A | 8/2000 | Duysens et al. | |
| 6,120,503 A | 9/2000 | Michelson | |
| 6,126,660 A | 10/2000 | Dietz | |
| 6,132,386 A | 10/2000 | Gozani et al. | |
| 6,132,387 A | 10/2000 | Gozani et al. | |
| 6,135,965 A | 10/2000 | Tumer et al. | |
| 6,139,493 A | 10/2000 | Koros et al. | |
| 6,146,335 A | 11/2000 | Gozani | |
| 6,152,871 A | 11/2000 | Foley et al. | |
| 6,181,961 B1 | 1/2001 | Prass | |
| 6,196,969 B1 | 3/2001 | Bester et al. | |
| 6,206,826 B1 | 3/2001 | Mathews et al. | |
| 6,224,549 B1 | 5/2001 | Drongelen | |
| 6,259,945 B1 | 7/2001 | Epstein et al. | |
| 6,266,558 B1 | 7/2001 | Gozani et al. | |
| 6,273,905 B1 | 8/2001 | Streeter | |
| 6,292,701 B1 | 9/2001 | Prass et al. | |
| 6,306,100 B1 | 10/2001 | Prass | |
| 6,312,392 B1 | 11/2001 | Herzon | |
| 6,325,764 B1 | 12/2001 | Griffith et al. | |
| 6,334,068 B1 | 12/2001 | Hacker | |
| 6,425,859 B1 | 7/2002 | Foley et al. | |
| 6,425,901 B1 | 7/2002 | Zhu et al. | |
| 6,451,015 B1 | 9/2002 | Rittman, III et al. | |
| 6,466,817 B1 | 10/2002 | Kaula et al. | |
| 6,468,205 B1 | 10/2002 | Mollenauer et al. | |
| 6,468,207 B1 | 10/2002 | Fowler, Jr. | |
| 6,500,128 B2 | 12/2002 | Marino | |
| 6,524,320 B2 | 2/2003 | DiPoto | |
| 6,535,759 B1 | 3/2003 | Epstein et al. | |
| 6,564,078 B1 | 5/2003 | Marino et al. | |
| 6,579,244 B2 | 6/2003 | Goodwin | |
| 6,620,157 B1 | 9/2003 | Dabney et al. | |
| 6,719,692 B2 | 4/2004 | Kleffner et al. | |
| 6,760,616 B2 | 7/2004 | Hoey et al. | |
| 6,796,985 B2 | 9/2004 | Bolger et al. | |
| 6,810,281 B2 | 10/2004 | Brock et al. | |
| 6,847,849 B2 | 1/2005 | Mamo et al. | |
| 6,849,047 B2 | 2/2005 | Goodwin | |
| 6,855,105 B2 | 2/2005 | Jackson, III et al. | |
| 6,902,569 B2 | 6/2005 | Parmer et al. | |
| 6,926,728 B2 | 8/2005 | Zucherman et al. | |
| 6,929,606 B2 | 8/2005 | Ritland | |

| | | | |
|---|---|---|---|
| 6,945,933 | B2 | 9/2005 | Branch |
| 7,047,082 | B1 | 5/2006 | Schrom et al. |
| 7,050,848 | B2 | 5/2006 | Hoey et al. |
| 7,079,883 | B2 * | 7/2006 | Marino et al. ............... 600/373 |
| 7,089,059 | B1 | 8/2006 | Pless |
| 7,177,677 | B2 | 2/2007 | Kaula et al. |
| 7,207,949 | B2 | 4/2007 | Miles et al. |
| 7,226,451 | B2 * | 6/2007 | Shluzas et al. ............. 606/86 R |
| 7,261,688 | B2 | 8/2007 | Smith et al. |
| 7,582,058 | B1 | 9/2009 | Miles et al. |
| 7,962,191 | B2 * | 6/2011 | Marino et al. ............... 600/373 |
| 2001/0039949 | A1 | 11/2001 | Loubser |
| 2001/0056280 | A1 | 12/2001 | Underwood et al. |
| 2002/0007129 | A1 | 1/2002 | Marino |
| 2002/0010392 | A1 | 1/2002 | Desai |
| 2002/0072686 | A1 | 6/2002 | Hoey et al. |
| 2002/0123780 | A1 | 9/2002 | Grill et al. |
| 2002/0161415 | A1 | 10/2002 | Cohen et al. |
| 2002/0193843 | A1 | 12/2002 | Hill et al. |
| 2003/0032966 | A1 | 2/2003 | Foley et al. |
| 2003/0105503 | A1 | 6/2003 | Marino |
| 2003/0149341 | A1 | 8/2003 | Clifton |
| 2003/0225405 | A1 | 12/2003 | Weiner |
| 2004/0225228 | A1 | 11/2004 | Ferree |
| 2005/0004593 | A1 | 1/2005 | Simonson |
| 2005/0004623 | A1 | 1/2005 | Miles et al. |
| 2005/0033380 | A1 | 2/2005 | Tanner et al. |
| 2005/0075578 | A1 | 4/2005 | Gharib et al. |
| 2005/0149035 | A1 | 7/2005 | Pimenta et al. |
| 2005/0182454 | A1 | 8/2005 | Gharib et al. |
| 2005/0192575 | A1 | 9/2005 | Pacheco |
| 2006/0025703 | A1 | 2/2006 | Miles et al. |
| 2006/0052828 | A1 | 3/2006 | Kim et al. |
| 2006/0069315 | A1 | 3/2006 | Miles et al. |
| 2006/0224078 | A1 | 10/2006 | Hoey et al. |
| 2007/0016097 | A1 | 1/2007 | Farquhar et al. |
| 2007/0198062 | A1 | 8/2007 | Miles et al. |
| 2007/0293782 | A1 | 12/2007 | Marino |
| 2008/0058606 | A1 | 3/2008 | Miles et al. |
| 2008/0064976 | A1 | 3/2008 | Kelleher et al. |
| 2008/0064977 | A1 | 3/2008 | Kelleher et al. |
| 2008/0065178 | A1 | 3/2008 | Kelleher et al. |
| 2008/0071191 | A1 | 3/2008 | Kelleher et al. |
| 2008/0097164 | A1 | 4/2008 | Miles et al. |
| 2008/0300465 | A1 | 12/2008 | Feigenwinter et al. |
| 2009/0124860 | A1 | 5/2009 | Miles et al. |
| 2009/0138050 | A1 | 5/2009 | Ferree |
| 2009/0192403 | A1 | 7/2009 | Gharib et al. |
| 2009/0204016 | A1 | 8/2009 | Gharib et al. |

FOREIGN PATENT DOCUMENTS

| | | |
|---|---|---|
| EP | 0 972 538 | 1/2000 |
| FR | 2 795 624 | 1/2001 |
| WO | 00/38574 | 7/2000 |
| WO | 00/66217 | 11/2000 |
| WO | 00/67645 | 11/2000 |
| WO | 01/37728 | 5/2001 |
| WO | 02/054960 | 7/2002 |
| WO | 03/005887 | 1/2003 |
| WO | 03/026482 | 4/2003 |
| WO | 03/037170 | 5/2003 |
| WO | 2005/013805 | 2/2005 |
| WO | 2005/030318 | 4/2005 |
| WO | 2006/042241 | 4/2006 |
| WO | 2006/066217 | 6/2006 |

OTHER PUBLICATIONS

Dirksmeier et al., "Microendoscopic and Open Laminotomy and Discectomy in Lumbar Disc Disease" *Seminars in Spine Surgery*, 1999, 11(2): 138-146.
METRx Delivered Order Form, 1999, 13 pages.
Medtronic Sofamor Danek "METRx™ MicroDisectomy System," *Medtronic Sofamor Danek USA*, 2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.
Japanese Patent Office JP Patent Application No. 2006-528306 Office Action with English Translation, Jun. 10, 2009, 4 pages.
Plaintiffs' Preliminary Invalidity Contentions re US Patents 7207949; 7470236 and 7582058, Sep. 18, 2009, 19 pages.
Plaintiffs' Preliminary Invalidity Contentions-Appendices, Sep. 18, 2009, 191 pages.
Plaintiffs' Supplemental Preliminary Invalidity Contentions re US Patents 7207949, 7470236, and 7582058, Sep. 29, 2009, 21 pages.
Plaintiffs' Supplemental Preliminary Invalidity Contentions-Appendices, Sep. 29, 2009, 294 pages.
Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.
Medtronic Sofamor Danek "Union™ / Union-L™ Anterior & Lateral Impacted Fusion Devices: Clear choice of stabilization," *Medtronic Sofamor Danek*, 2000, 4 pages.
NuVasive Vector™ Cannulae, 1 page (prior to Sep. 25, 2003).
NuVasive Triad™ Tri-Columnar Spinal EndoArthrodesis™ via Minimally Invasive Guidance, 1 page (prior to Sep. 25, 2003).
NuVasive Triad™ Cortical Bone Allograft, 1 page (prior to Sep. 25, 2003).
NuVasive Vertebral Body Access System, 1 page (prior to Sep. 25, 2003).
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.
NuVasive letter re 510k INS-1 Intraoperative Nerve Surveillance System, Nov. 13, 2000, 7 pages.
"NuVasive™ Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
Isley et al., "Recent Advances in Intraoperative Neuromonitoring of Spinal Cord Function: Pedicle Screw Stimulation Techniques," *American Journal of Electroneurodagnostic Technology*, Jun. 1997, 37(2): 93-126.

Mathews et al., "Laparoscopic Discectomy with Anterior Lumbar Interbody Fusion," *Spine*, 1995, 20(16): 1797-1802.
Rose et al., "Persistently Electrified Pedicle Stimulation Instruments in Spinal Instrumentation: Techniques and Protocol Development," *Spine*, 1997, 22(3): 334-343.
"Electromyography System," International Search report from International Application No. PCT/US00/32329, Apr. 27, 2001, 9 pages.
"Nerve Proximity and Status Detection System and Method," International Search Report from International Application No. PCT/US01/18606, Oct. 18, 2001, 6 pages.
"Relative Nerve Movement and Status Detection System and Method," International Search Report from International Application No. PCT/US01/18579, Jan. 15, 2002, 6 pages.
"System and Method for Determining Nerve Proximity Direction and Pathology During Surgery," International Search Report from International Application No. PCT/US02/22247, Mar. 27, 2003, 4 pages.
"System and Methods for Determining Nerve Direction to a Surgical Instrument," International Search Report from International Application No. PCT/US03/02056, Aug. 12, 2003, 5 pages.
"Systems and Methods for Performing Percutaneous Pedicle Integrity Assessments," International Search Report from International Application No. PCT/US02/35047, Aug. 11, 2003, 5 pages.
"Systems and Methods for Performing Surgery Procedures and Assessments," International Search Report from International Application No. PCT/US02/30617, Jun. 5, 2003, 4 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.
Anderson et al., "Pedicle screws with high electrical resistance: a potential source of error with stimulus-evoked EMG," *Spine*, Department of Orthopaedic Surgery University of Virginia, Jul. 15, 2002, 27(14): 1577-1581.
Bose et al., "Neurophysiologic Monitoring of Spinal Nerve Root Function During Instrumented Posterior Lumber Spine Surgery," *Spine*, 2002, 27(13):1444-1450.
Calancie et al., "Stimulus-Evoked EMG Monitoring During Transpedicular Lumbosacral Spine Instrumentation" *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," *Spine*, Charlotte Spine Center North Carolina, Jan. 15, 1998, 23(2): 256-262.
Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.
Ford et al. "Electrical Characteristics of Peripheral Nerve Stimulators Implications for Nerve Localization," *Regional Anesthesia*, 1984, 9: 73-77.
Glassman et al., "A Prospective Analysis of Intraoperative Electromyographic Monitoring of Pedicle Screw Placement With Computed Tomographic Scan Confirmation," *Spine*, 1995, 20(12): 1375-1379.
Greenblatt et al., "Needle Nerve Stimulator-Locator: Nerve Blocks with a New Instrument for Locating Nerves," *Anesthesia& Analgesia*, 1962, 41(5): 599-602.
Haig, "Point of view," *Spine*, 2002, 27(24): 2819.

Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.
Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.
Holland, "Intraoperative Electromyography During Thoracolumbar Spinal Surgery," *Spine*, 1998, 23(17): 1915-1922.
Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I*, 18th Annual International Conference on Engineering in Medicine and Biology Society, Amsterdam, 1996, pp. 144-145.
Maguire et al., "Evaluation of Intrapedicular Screw Position Using Intraoperative Evoked Electromyography," *Spine*, 1995, 20(9): 1068-1074.
Martin et al. "Initiation of Erection and Semen Release by Rectal Probe Electrostimulation (RPE)," *The Journal of Urology*, The Williams& Wilkins Co., 1983, 129: 637-642.
Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.
Pither et al., "The Use of Peripheral Nerve Stimulators for Regional Anesthesia: Review of Experimental Characteristics Technique and Clinical Applications," *Regional Anesthesia*, 1985, 10:49-58.
Raj et al., "Infraclavicular Brachial Plexus Block—A New Approach" *Anesthesia and Analgesia*, 1973, (52)6: 897-904.
Raj et al., "The Use of Peripheral Nerve Stimulators for Regional Anesthesia," *Clinical Issues in Regional Anesthesia*, 1985, 1(4):1-6.
Raj et al., "Use of the Nerve Stimulator for Peripheral Blocks," *Regional Anesthesia*, Apr.-Jun. 1980, pp. 14-21.
Raymond et al., "The Nerve Seeker: A System for Automated Nerve Localization," *Regional Anesthesia*, 1992, 17(3): 151-162.
Shafik, "Cavernous Nerve Simulation through an Extrapelvic Subpubic Approach: Role in Penile Erection," *Eur. Urol*, 1994, 26: 98-102.
Toleikis et al., "The Usefulness of Electrical Stimulation for Assessing Pedicle Screw Replacements," *Journal of Spinal Disorder*, 2000, 13(4): 283-289.
Medtronic Sofamor Danek "Union™ / Union-L™ Anterior & Lateral Impacted Fusion Devices: Surgical Technique" *Medtronic Sofamor Danek*, 2001, 20 pages.
Defendant's Disclosure of Asserted Claims and Preliminary Infringement Contentions Regarding USP 7207949; 7470236 and 7582058, Aug. 31, 2009, 21 pages.
Bergey et al., "Endoscopic Lateral Transpsoas Approach to the Lumbar Spine," *Spine*, 2004, 29(15): 1681-1688.
Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.
Gardocki, "Tubular diskectomy minimizes collateral damage: A logical progression moves spine surgery forward," *AAOS Now*, 2009, 5 pages.
Hovorka et al., "Five years' experience of retroperitoneal lumbar and thoracolumbar surgery," *Eur Spine J.*, 2000, 9(1): S30-S34.
Kossman et al., "The use of a retractor system (SynFrame) for open, minimal invasive reconstruction of the anterior column of the thoracic and lumbar spine," *Eur Spine J.*, 2001, 10: 396-402.
Mayer, "A New Microsurgical Technique for Minimally Invasive Anterior Lumbar Interbody Fusion," *Spine*, 1997, 22(6): 691-699.
Mayer, "The ALIF Concept," *Eur Spine J.*, 2000, 9(1): S35-S43.
Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Wolfla, Christopher E. et al., "Retropritoneal Lateral Lumbar Interbody Fusion with Titanium Threade Fusion Cages," J. Neurosurg (Spine 1), 2002, 96: 50-55.

Larson, Sanford J. et al., "Surgery of the Lumbar Spine," 1999, pp. 305-319.

Medtronic Xomed Surgical Products, Inc. "NIM-Response Nerve Integrity Monitor Intraoperative EMG Monitor User's Guide, Revision B," 2000.

* cited by examiner

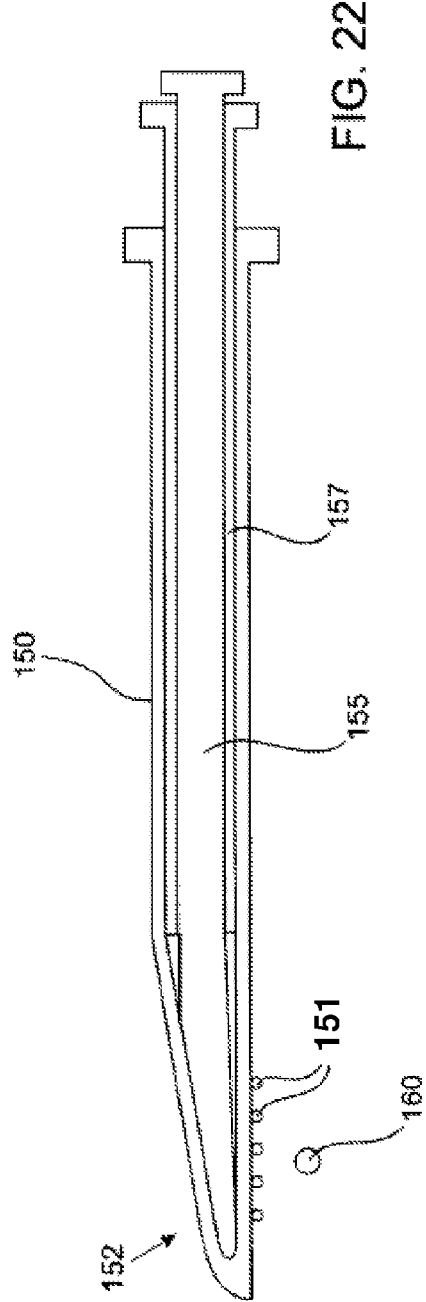
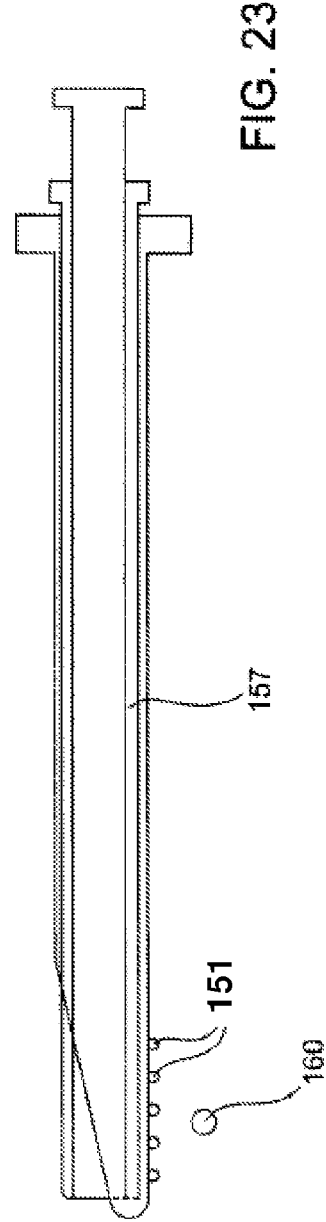

SURGICAL ACCESS AND NERVE SURVEILLANCE

CROSS-REFERENCES TO RELATED APPLICATIONS

The present application is a continuation of U.S. application Ser. No. 11/982,254, filed Oct. 31, 2007 and now issued as U.S. Pat. No. 7,962,191, which is a continuation of U.S. patent application Ser. No. 11/489,020, filed Jul. 18, 2006, which is a divisional of U.S. application Ser. No. 10/431,619, filed May 7, 2003 and now issued as U.S. Pat. No. 7,079,883, which is a divisional of U.S. patent application Ser. No. 09/325,998, filed Jun. 4, 1999 and now issued as U.S Pat. No. 6,564,078, which claims benefit under 35 U.S.C. §119(e) from U.S. Provisional Patent Applications Ser. No. 60/113,651 filed Dec. 23, 1998; U.S. Provisional Patent Application Ser. No. 60/120,663 filed Feb. 19, 1999; and U.S. Provisional Patent Application Ser. No. 60/123,268 filed Mar. 8, 1999; the complete disclosures of which are hereby incorporated herein by reference in their entirety for all purposes.

BACKGROUND OF THE INVENTION

I. Field of the Invention

The present invention relates to nerve surveillance systems and to cannulae systems for use in minimally invasive spinal surgery.

II. Discussion of the Prior Art

A significant danger of performing intervertebral operations or accessing an intervertebral space during spine surgery is that of inadvertently contacting or damaging the para-spinal nerves, including the exiting nerve roots, traversing nerves and the nerves of the cauda equina. The exact location of these para-spinal nerves cannot be determined prior to the commencement of surgery. Moreover, intervertebral spaces in the spine have other sensitive nerves disposed at locations which are not entirely predictable prior to insertion of the surgical tool into the intervertebral area. Accordingly, the danger of pinching or damaging spinal nerves when accessing an intervertebral space has proven to be quite limiting to the methods and devices used during minimally invasive spinal surgery. In addition, as cannulae are received through the patient's back, such as when performing minimally invasive spinal surgery, minor blood vessels are ruptured, thereby blocking the surgeon's vision inside the intervertebral region after the cannula has been inserted.

SUMMARY OF THE INVENTION

The present invention provides nerve surveillance probes which are adapted to assist the surgeon in identifying the presence and location of para-spinal nerves as the probe is advanced during minimally-invasive surgery, thus providing a device for guiding the path of other surgical instruments to be inserted into this intervertebral space. In a preferred aspect of the present invention, an expandable tip cannula system is provided which functions both as an access portal for spinal surgery and as a system for nerve surveillance such that the presence and relative position of para-spinal nerves can be detected as the expandable tip cannula is inserted through the patient's facia and para-spinal musculature. An advantage of determining the position of the para-spinal nerve with respect to the distal tip of the cannula in particular is that the para-spinal nerve can be avoided or gently moved out of the surgeon's way while inserting the cannula. Accordingly, in a preferred aspect, the present invention provides a cannulated system which is adapted to assist the surgeon in guiding the path of surgical instruments received into the intervertebral space, while identifying the presence and location of para-spinal nerves as the cannula is advanced to a patient's intervertebral space during minimally invasive surgery.

Optionally, the present nerve surveillance expandable tip cannula may also be adapted to selectively electrically induce cauterization of severed blood vessels when the cannula or other surgical instruments sever small blood vessels when they are inserted percutaneously into the patient and are advanced along a path into the patient's intervertebral space. An additional advantage of the present cannula system therefore is that, prior to piercing the annulus of an intervertebral disc, vessels on the surface of the disc may be cauterized to assure clear vision inside the disc after surgical entry is made.

In one embodiment, the present expandable tip nerve surveillance cannula preferably comprises a hollow tubular body with an expandable tip portion mounted at its distal end. In a preferred aspect of the invention, the expandable tip portion comprises a plurality of generally triangular shaped petals which are held together in a radially-inwardly tapering arrangement by breakable seals disposed between adjacent petals. Since the expandable tip portion of the cannula tapers to a narrow blunt end, the cannula can be easily pushed through the patient's facia and spinal musculature using blunt dissection, while minimizing the amount of cutting and tearing of such structures.

Alternatively, a central electrode can be disposed on a central obturator passing though the cannula and a second electrode can be disposed on a distal end of a second cannula, wherein the second cannula is used to open the petals.

An obturator shaft which is slidably received within the hollow tubular cannula body provides support for the cannula, giving the cannula sufficient strength such that the cannula can be inserted percutaneously through the patient's facia and para-spinal musculature. Preferably, the obturator has a large solid handle which allows the surgeon to grasp and push the cannula through the resistance of the facia and para-spinal musculature.

After the cannula has been inserted and is resting on the patient's annulus, an inner cannula or rod which is slidably received within the cannula is then used to separate the breakable seals, opening the petals radially outwards to a distance sufficient to provide access for surgical instruments passing therethrough.

In some preferred aspects, an electrode is disposed in each of the petals, and most preferably at or near the distal end of each of the petals. In other aspects of the invention, a plurality of electrodes are radially disposed about the distal end of the obturator and the electrodes protrude out of a small hole defined by truncated petals, as will be explained.

In various aspects of the present invention, the electrodes can be powered at a low level to thereby sense the position of a para-spinal nerve through continuous real time electromyographic monitoring, or alternatively, the electrodes can be powered at a higher level such that they operate to cauterize blood vessels. Safety systems ensure that power levels sufficient to cause cauterization are not activated if a nerve is sensed to be near the electrodes at the distal end of the cannula.

In alternate embodiments, the present invention comprises an elongated nerve surveillance probe having one or more electrodes at its distal tip. In such aspects, the nerve surveillance probe is preferably advanced to the patient's intervertebral space through a cannula. In other alternate embodiments, the present nerve surveillance probe is received into the patient through various cannulae and expandable mesh trocars.

BRIEF DESCRIPTION OF THE DRAWINGS

FIG. 22 is a side sectional view of the peel back cannula of FIG. 20 in a sealed position.

FIG. 23 is a sectional side elevation view of the peel back cannula of FIG. 20 in an open position.

DESCRIPTION OF THE PREFERRED EMBODIMENT

As will be set forth herein, the present invention encompasses both nerve surveillance probes which are received through cannulae, and various expandable tip cannulae comprising nerve surveillance probes at their distal ends.

Figure 1:
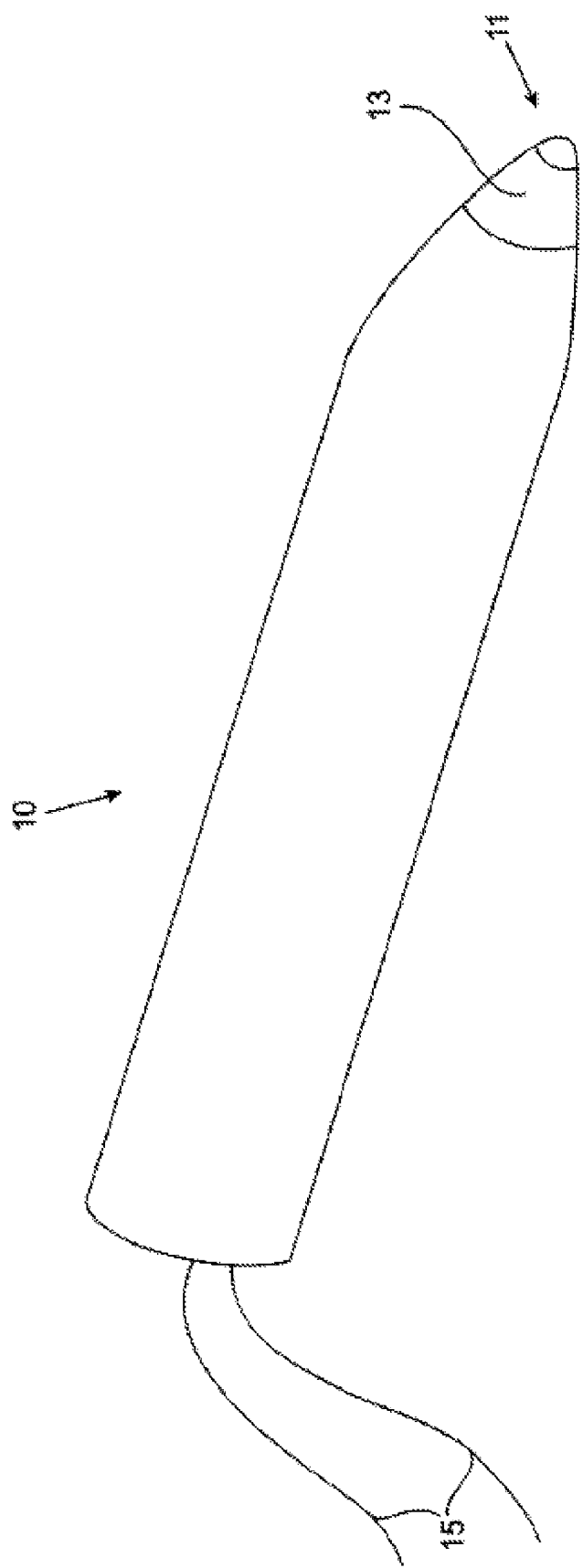
FIG. 1 is a side perspective view of a first nerve surveillance probe of the present invention.
Figure 2:
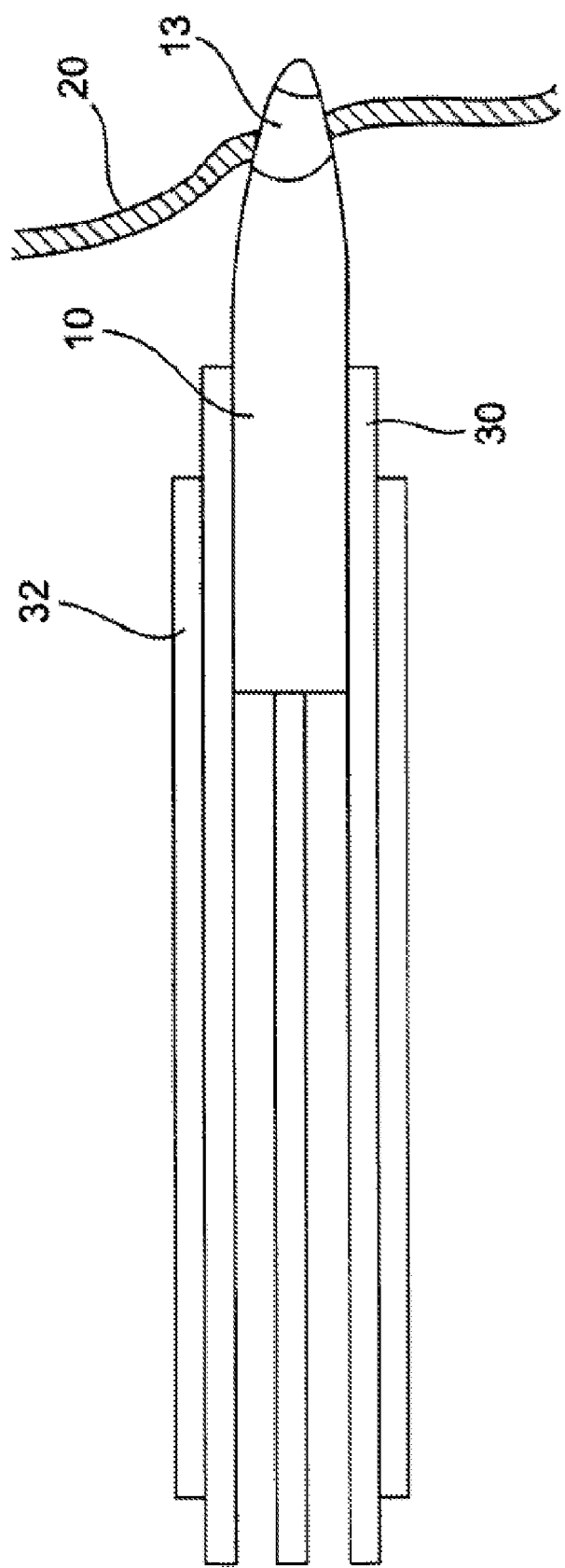
FIG. 2 is a sectional side elevation view of the first nerve surveillance probe positioned adjacent the spinal nerve with the first probe received within a first cannula which is itself received with an expandable mesh.

In a first preferred embodiment, as is seen in FIG. 1, an electromyography nerve surveillance probe 10 having a blunt end 11 is provided. Electrode 13 is disposed at the distal end of probe 10 and is charged by electrical contacts 15. As electrode 13 approaches nerve 20 (as seen in FIG. 2), the minimal threshold depolarization value elicited by the electrode will result in corresponding electromyography activity, such that the presence of nerve 20 can be sensed by standard electromyographic techniques, thus indicating the presence of the nerve. Specifically, using standard electromyographic techniques, the presence of nerve 20 will be sensed by appropriate needles or patches attached to the appropriate muscle as electrode 13 stimulates, and thereby depolarizes nerve 20.

In an exemplary method of application, (as is shown in FIG. 2), the present nerve surveillance probe 10 can be advanced percutaneously through the patient's back in a posterolateral approach towards the patient's intervertebral space using the arrangement in which a first cannula 30 surrounds probe 10 as the probe is advanced. As probe 10 is advanced, it will then become positioned proximal nerve 20. When this occurs, the presence of nerve 20 relative to probe 10 will be determined by the signal generated by electrode 13 as set forth above.

Figure 3:
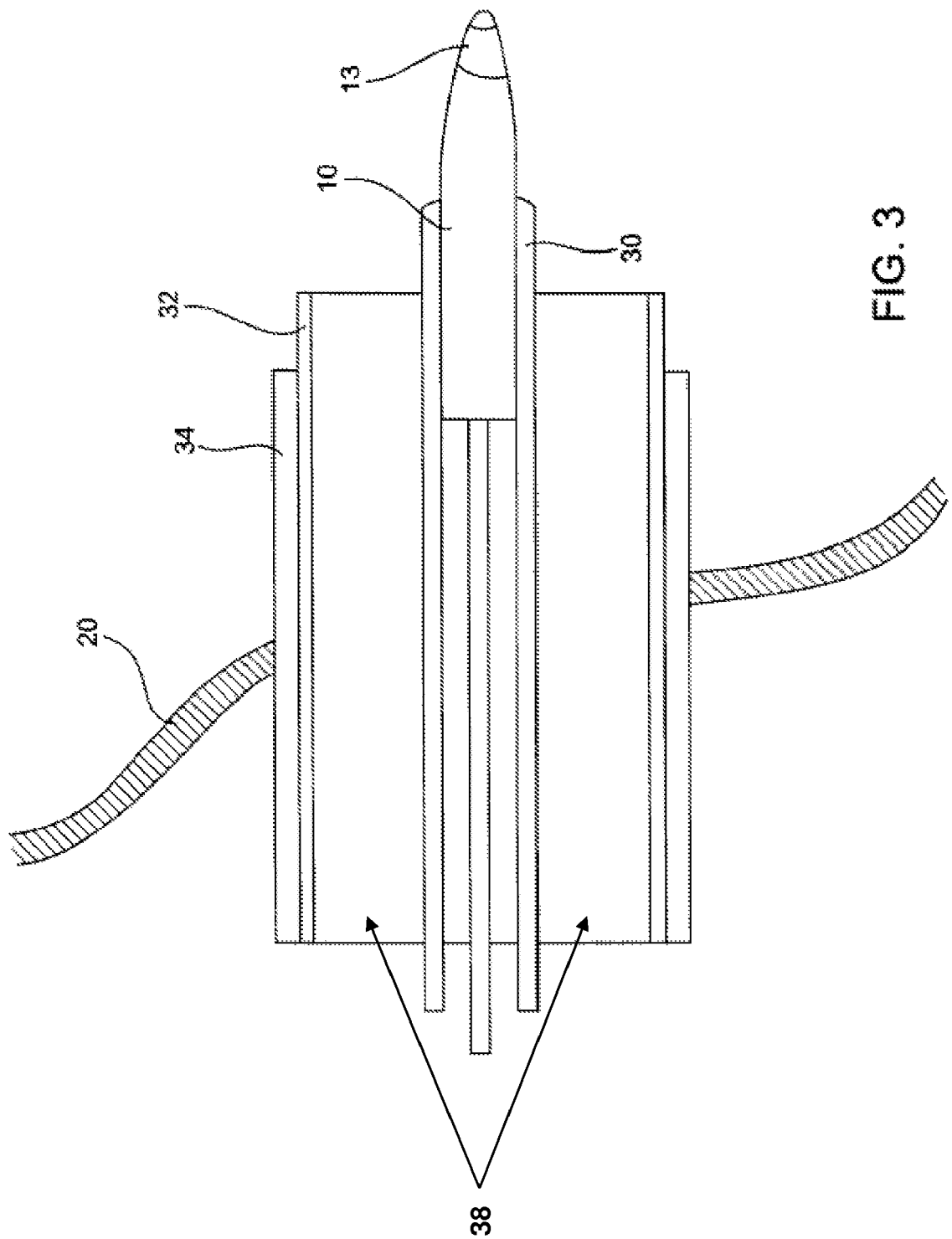
FIG. 3 shows the probe of FIG. 2, but with the mesh expanded and a second cannula received thereover, (after the distal ends of the first cannula and expandable mesh have been advanced past the nerve).

In one preferred aspect of the present invention, an expandable mesh 32 is received over first cannula 30 such that expansion of this mesh from the contracted position shown in FIG. 2 to the expanded position shown in FIG. 3 will gently move nerve 20 out of the way.

Figure 4:
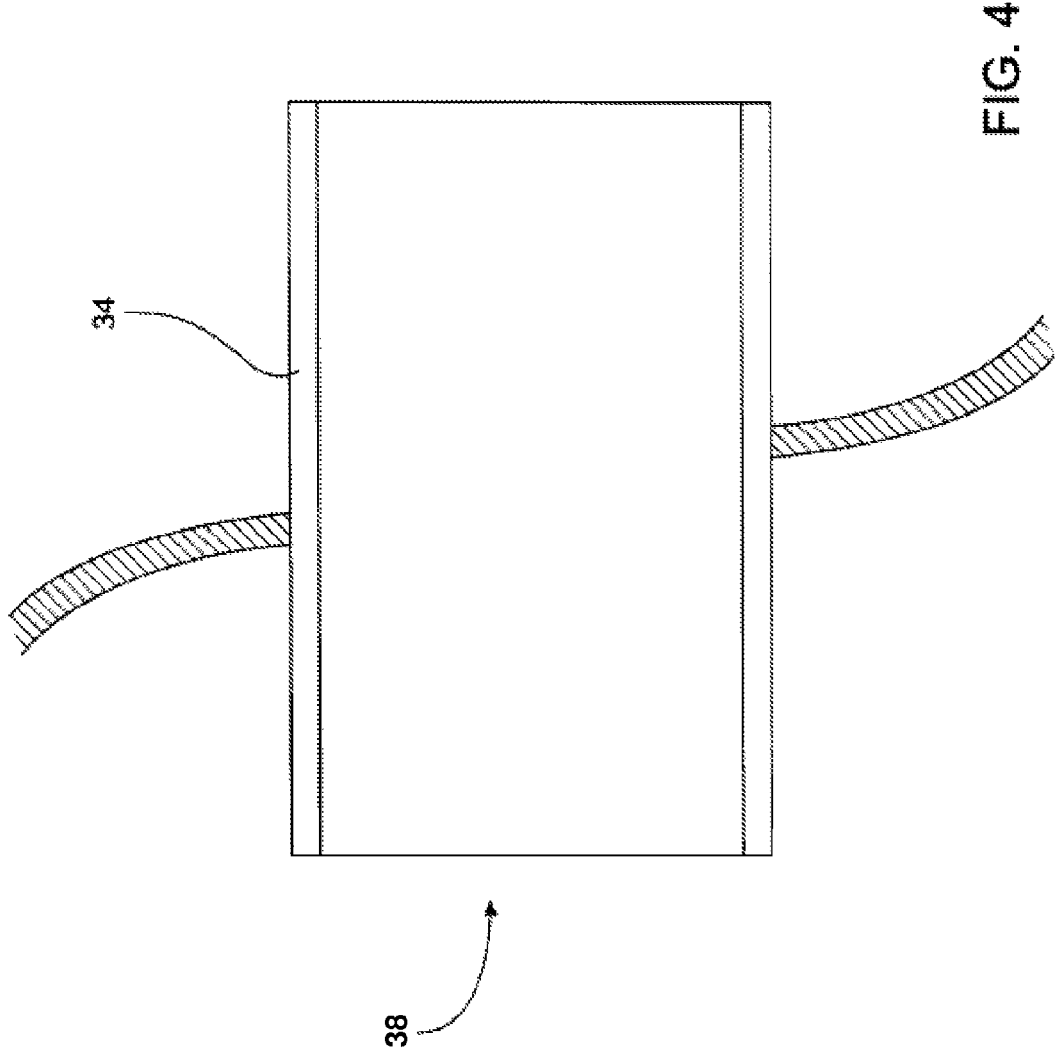
FIG. 4 is a sectional side elevation corresponding to FIG. 3, but with the first probe and first cannula removed.
Figure 5:
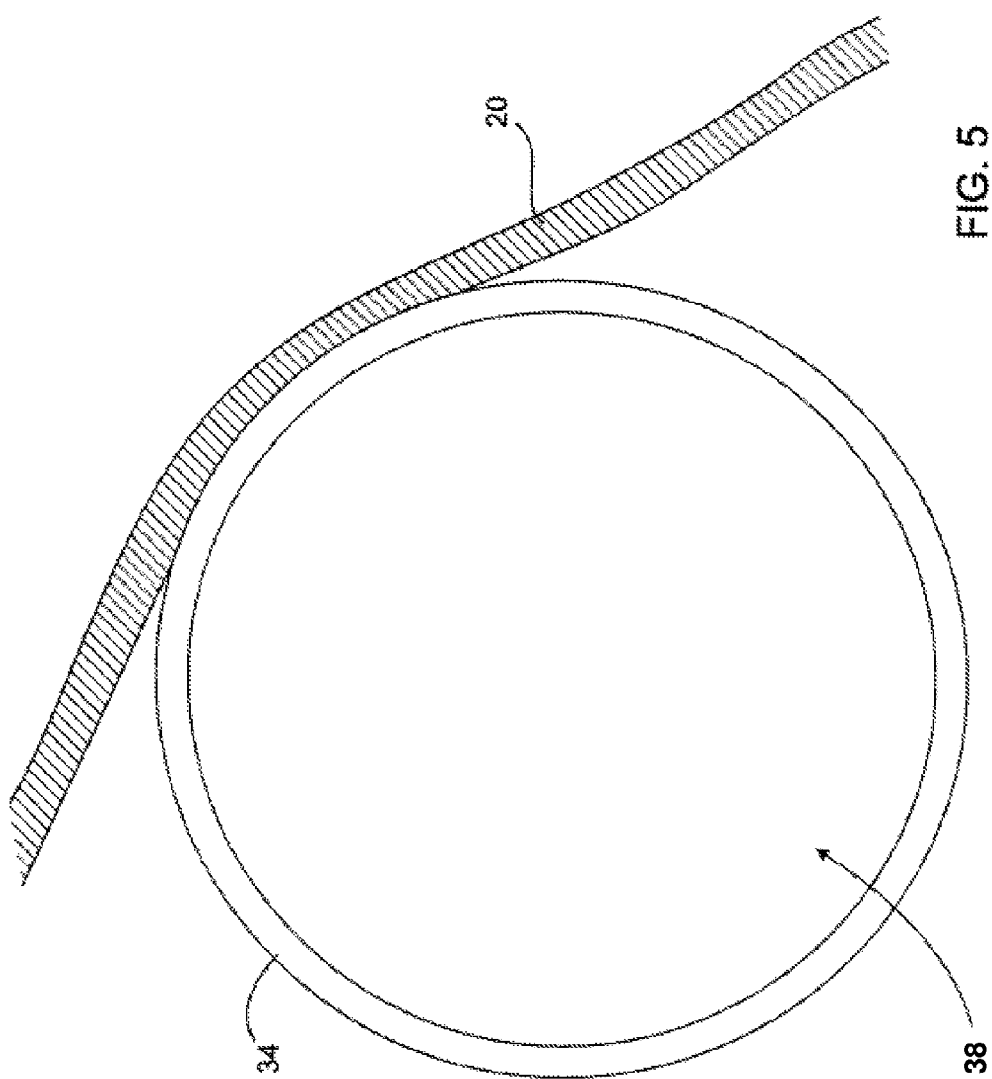
FIG. 5 is an end view corresponding to FIG. 4.

Also in a preferred aspect as shown in FIG. 3, a second cannula 34 can thereafter be received over expanded mesh 32, thereby providing a large passageway 38 for intervertebral access when probe 10, first cannula 30, and expanded mesh 32 are removed as shown in FIGS. 4 and 5. Accordingly, the large passageway 38 into the intervertebral area provided by cannula 34 protects sensitive nerve 20 while providing access for surgical instruments therethrough, including such surgical instruments as intervertebral inserts, bone decorticators, cameras, articulating forceps, intervertebral inserts and intervertebral positioning systems.

Figure 6:
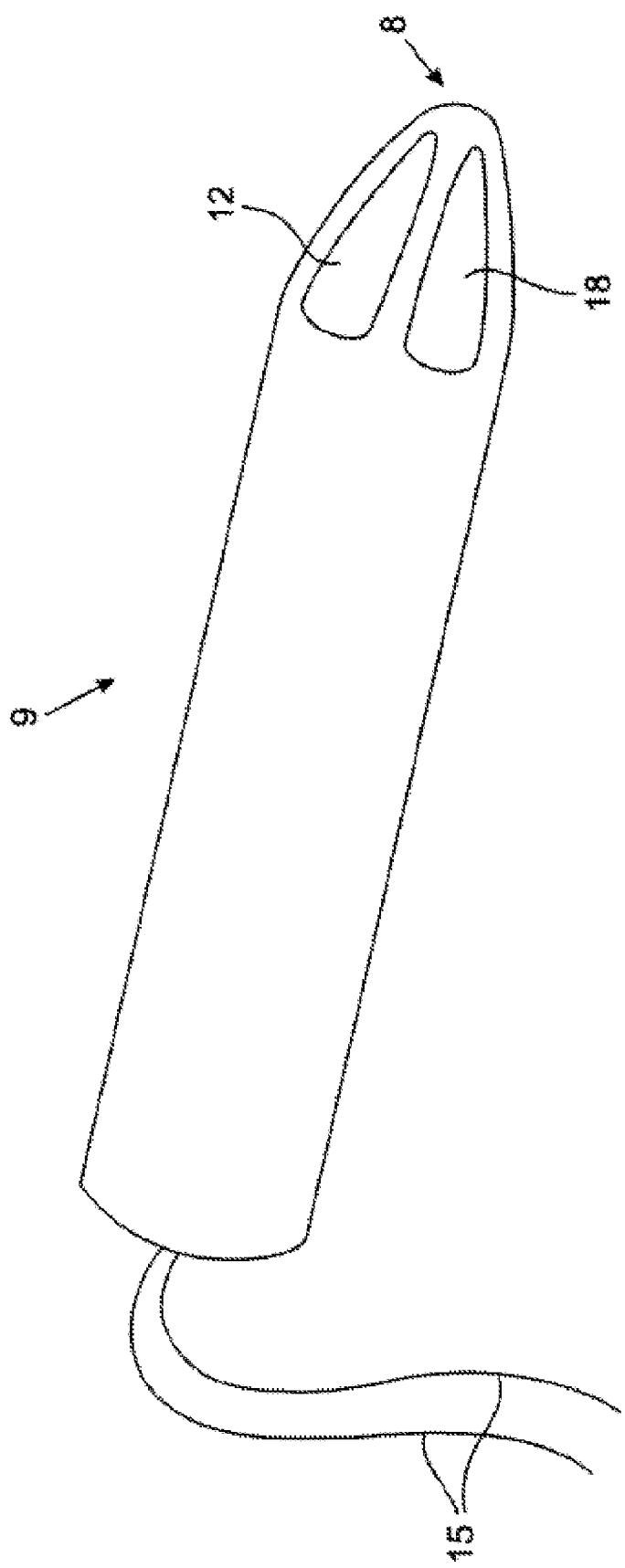
FIG. 6 is a side perspective view of a second nerve surveillance probe of the present invention.
Figure 7:
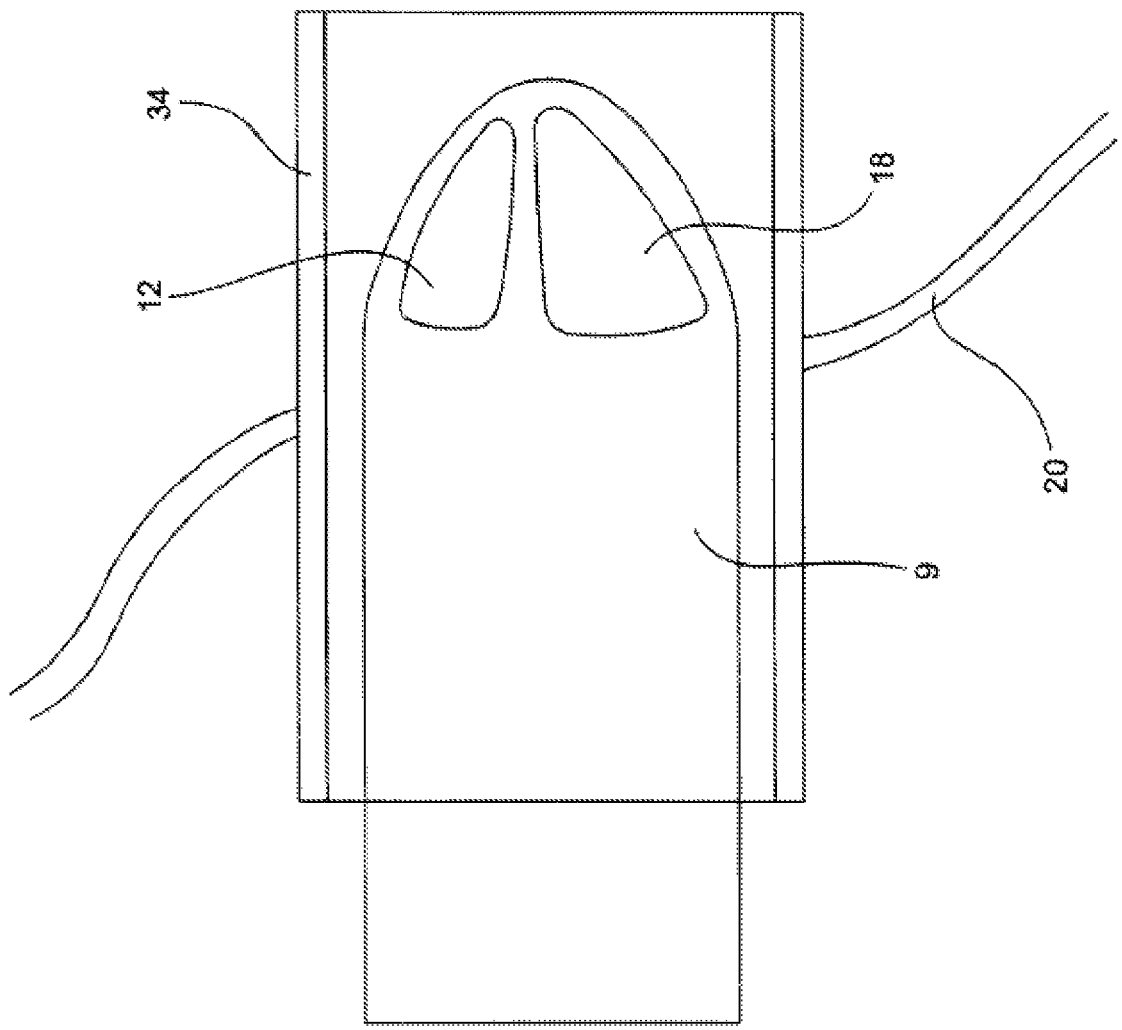
FIG. 7 is a sectional side elevation view of a second nerve surveillance probe received within the second cannula.
Figure 8:
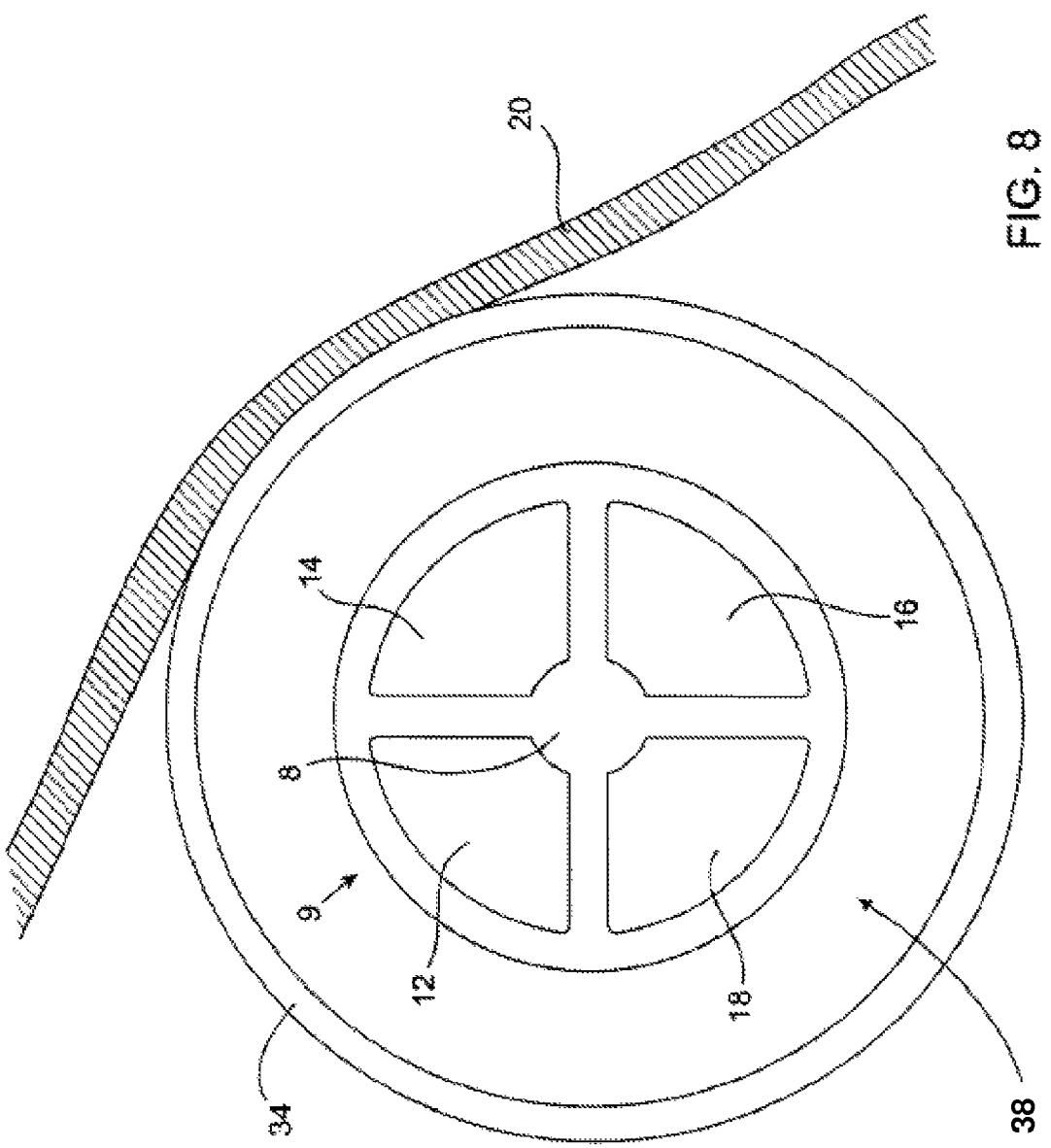
FIG. 8 is an end view corresponding to FIG. 7.

As is seen in FIG. 6, a second nerve surveillance probe 9 is also provided. Nerve surveillance probe 9 has a plurality of electrodes 12, 14, 16 and 18 disposed at radial locations adjacent to blunt distal end 8, as is seen in FIGS. 6, 7 and 8. Radially disposed electrodes 12, 14, 16, and 18 perform a variety of useful functions, as follows.

Referring to FIG. 8, as electrodes 12, 14, 16, and 18 are disposed at radial locations around the tip of probe 10, the electrodes which are closest to nerve 20, (in this case electrode 14, and to a lesser degree electrodes 12 and 16), will operate to depolarize the nerve such that the presence of nerve 20 can be detected by standard electromyographic techniques. As such, a signal will be generated telling the operating surgeon that nerve 20 is proximal to electrode 14. As can be appreciated, should nerve 20 instead be positioned in another orientation, the signal from electrodes 12, 14, 16 and 18 would instead indicate the presence of the nerve at a different location. Accordingly, probe 9 can be operated as a tool for inspecting the interior passageway of cannula 34 to determine if nerve 20 had become inadvertently trapped therein as cannulae 34 is advanced over expanded mesh 32. Moreover, as the electrodes 12, 14, 16, and 18 are disposed at radial locations around the distal end of the probe, it is possible to determine the exact location of nerve 20. Preferably as well, each of electrodes 12, 14, 16, and 18 will be activated in a repeating sequence with a sufficient delay time therebetween to detect an electromyographic response.

In another aspect of the invention, radially disposed electrodes 12, 14, 16, and 18 can be used for electrocoagulation of blood vessels, for example, blood vessels on the patient's annulus when accessing the patient's intervertebral region. Specifically, as a plurality of electrodes are disposed at the distal end of probe 9, it is possible to pass current between various electrodes, thus cauterizing adjacent blood vessels.

Figure 10:
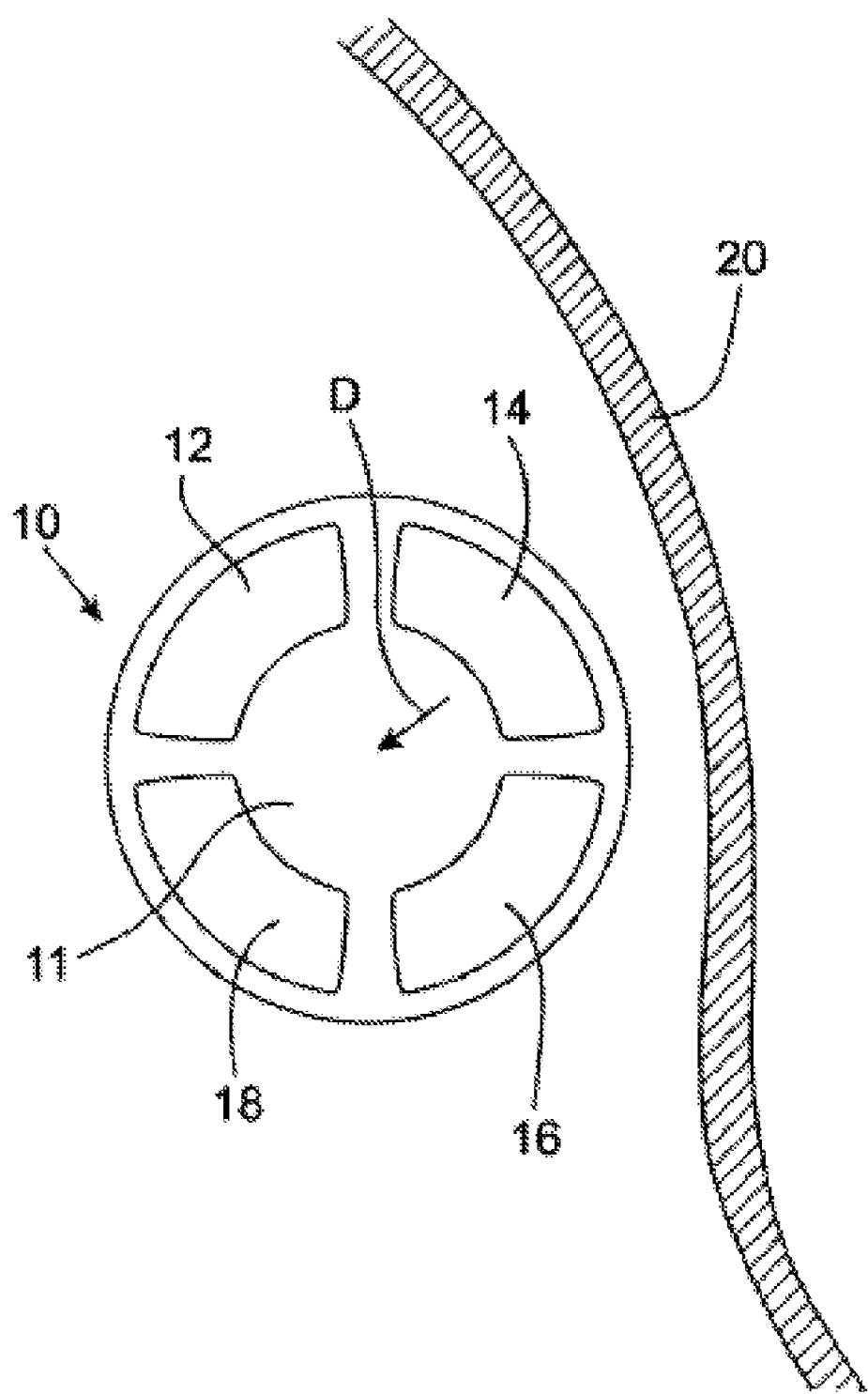
FIG. 10 is an end view of the nerve surveillance probe of FIG. 6 pushing a nerve out of the way of an advancing cannula.

In another aspect of the invention, radially disposed electrodes 12, 14, 16, and 18 can be used to assist in avoiding, or alternatively in moving, nerve 20 as follows. Referring to FIG. 10, nerve 20 will be determined to be adjacent to electrode 14 using the above set forth method. Probe 10 can then be gently moved in a radial direction away from electrode 14, as is shown by arrow D, such that nerve 20 can then be gently pushed out of the way, providing safe access to the patient's intervertebral space. Alternatively, the movement of probe 10 in a direction opposite direction D will push the nerve out of the way such that a cannula can then be advanced past nerve 20 without damaging the nerve.

Figure 9A:
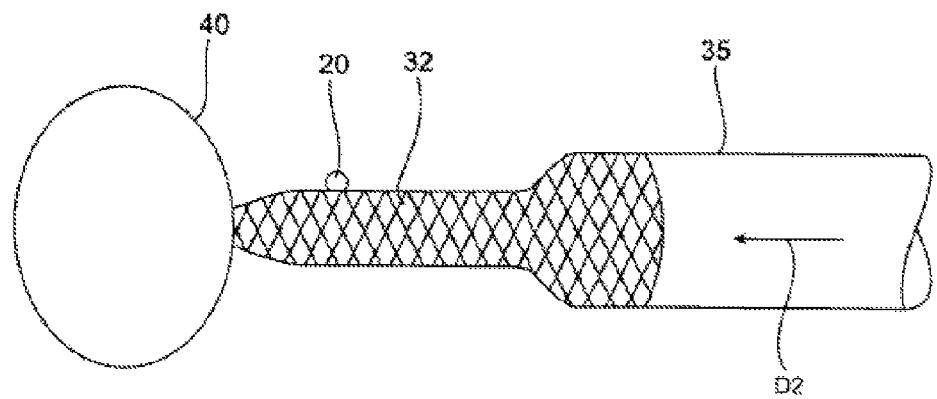
FIG. 9A, 9B and 9C sequentially show a schematic view of an expandable mesh system as moved from a contracted position (FIG. 9A) to an expanded position (FIG. 9B), and with an outer cannula received thereover (FIG. 9C).
Figure 9B:
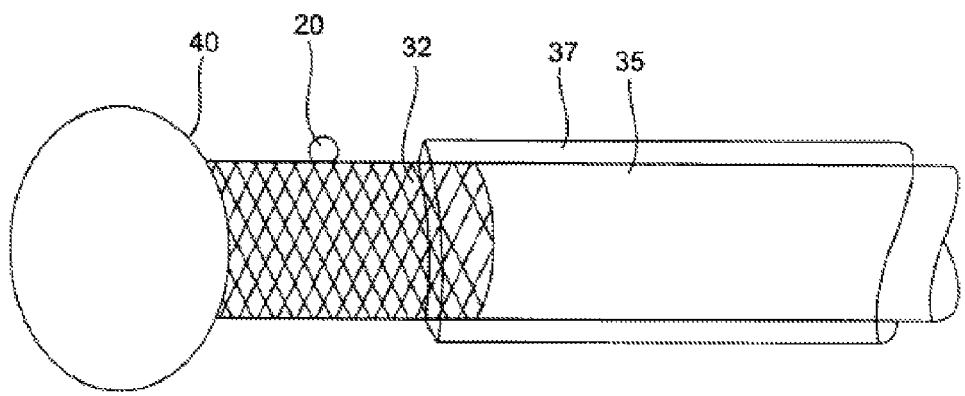
Figure 9C:
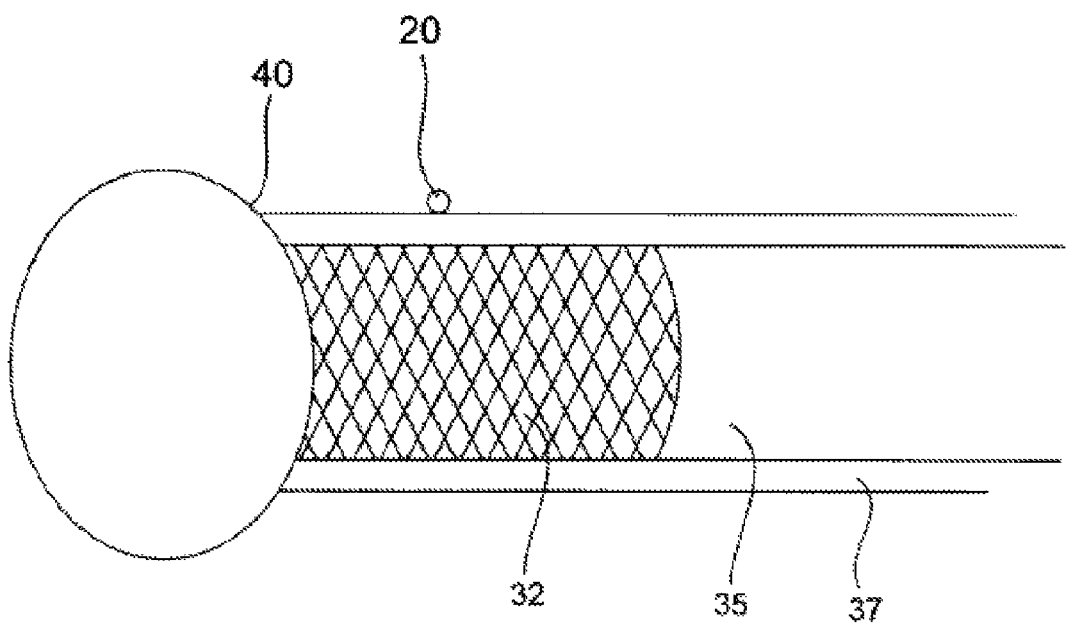

In another aspect of the present invention as shown in FIGS. 9A, 9B and 9C, the expansion of mesh 32 is controlled as follows. As is shown in FIG. 9A, expandable mesh 32 is in a contracted position and is mounted on the end of a cannula 35. A distal end of mesh 32 is positioned against the patient's annulus 40 or any other suitably hard bone structure. Pushing rod or cannula 35 in direction D2 will compress mesh 32, causing it to expand radially and shorten. This movement will displace nerve 20 (shown here in cross section). Following this, cannula 37 can be slid over expanded mesh 32 is seen in FIG. 9B. Following this, cannula 37 can be advanced past nerve 20, gently pushing nerve 20 still further out of the way, as shown in FIG. 9C. Lastly, rod or cannula 35 and attached mesh 32 can be removed, leaving a large cannulated passageway to the annulus or intervertebral space.

It is to be understood that the present nerve surveillance probes can be used without the expandable mesh system of FIGS. 9A, 9B and 9C. Moreover, it is to be understood that the present method and apparatus of minimally invasive nerve surveillance can be used in any arthroscopic procedure.

As can also be appreciated the present nerve surveillance probes are able to detect the presence of any other efferent skeletal motor nerve in addition to the spinal nerve and can thus be used in various surgical procedures. Alternatively, using evoked potential electromyography, the present nerve surveillance probes are also adapted to sense the presence of afferent sensory nerves in response to signals received in the spinal cord or cerebral cortex.

Figure 12:
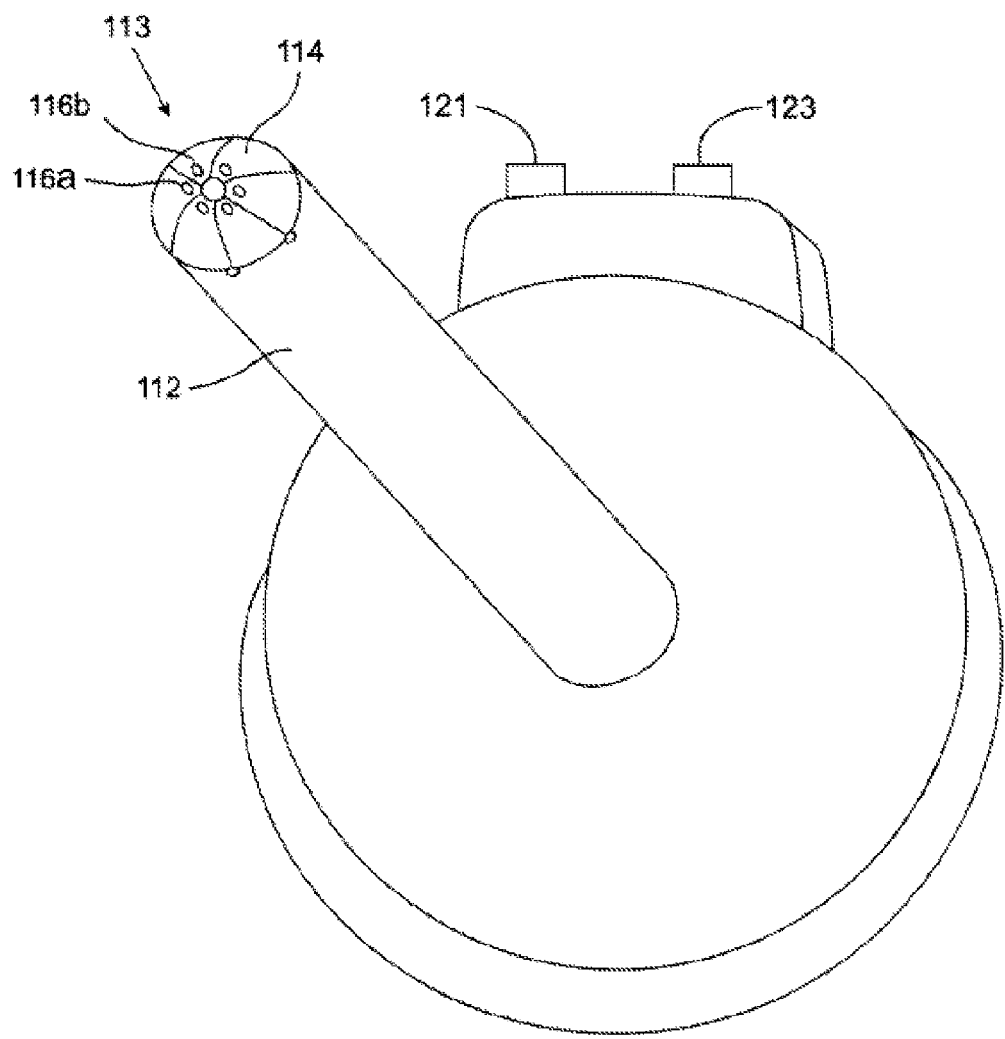
FIG. 12 is a perspective distal view of the system of FIG. 11.
Figure 13:
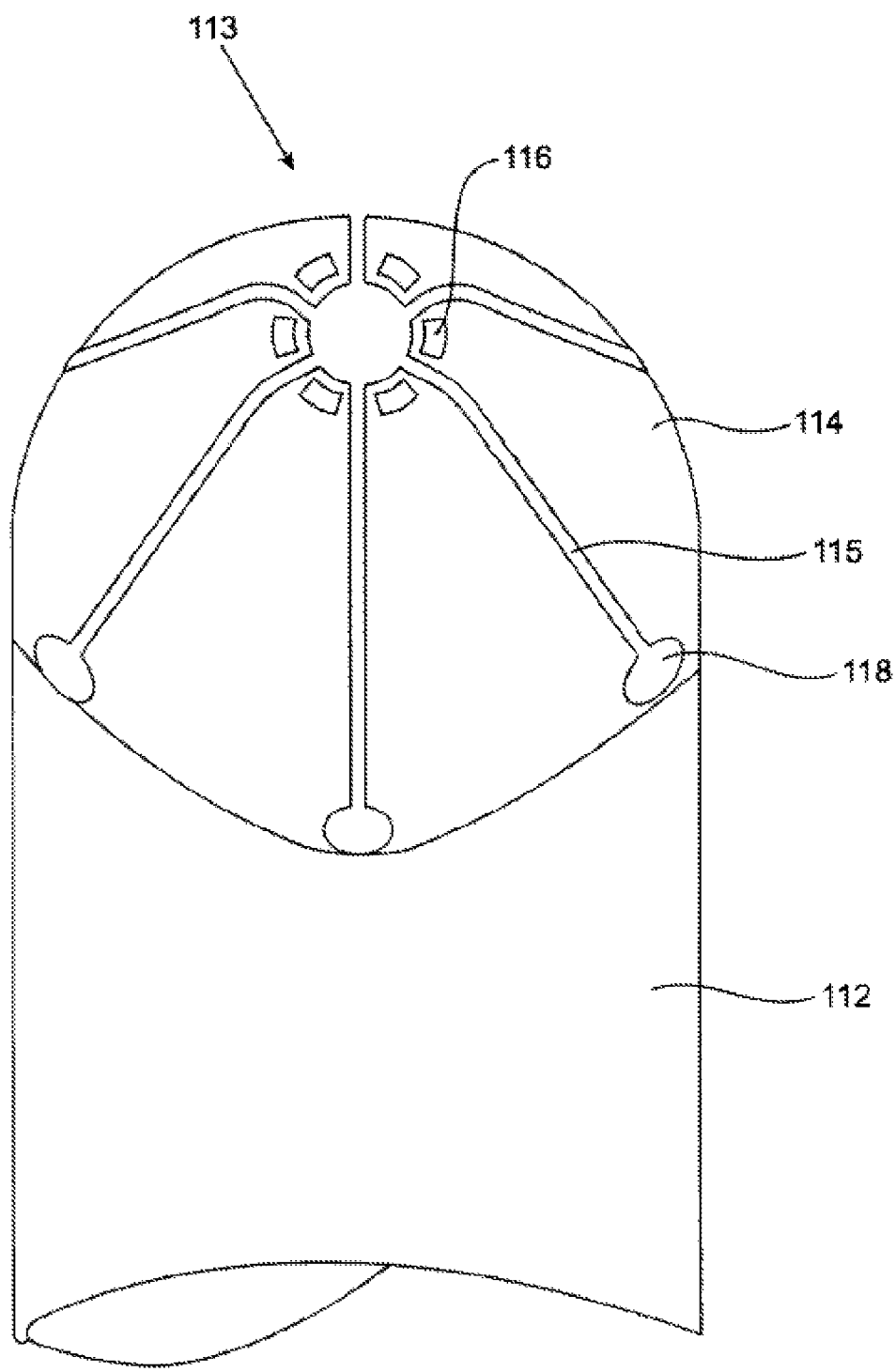
FIG. 13 is a view of the distal tip of the system of FIG. 12, with the petals in a closed position.
Figure 14:
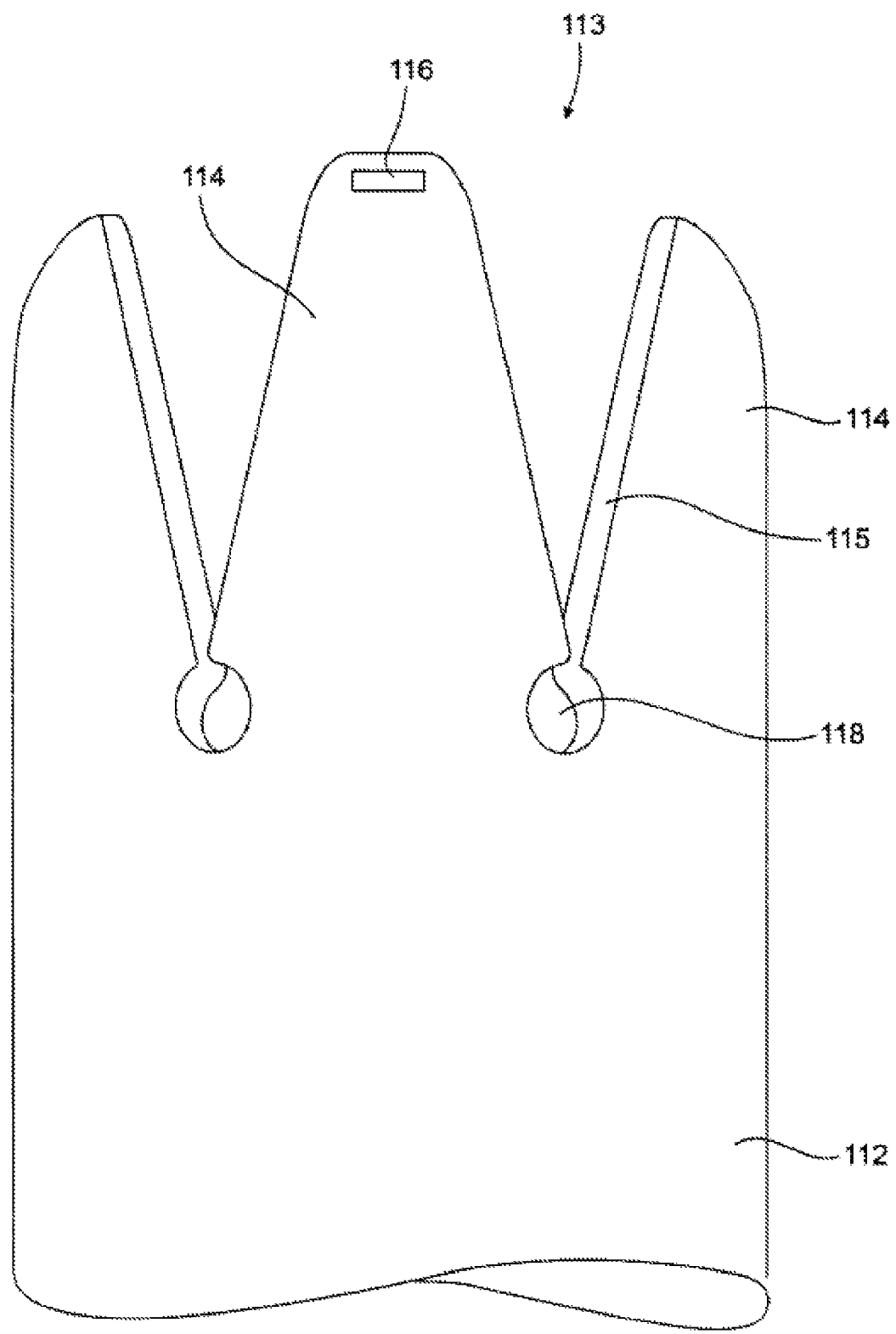
FIG. 14 is a view corresponding to FIG. 13, but with petals in an open position.
Figure 15:
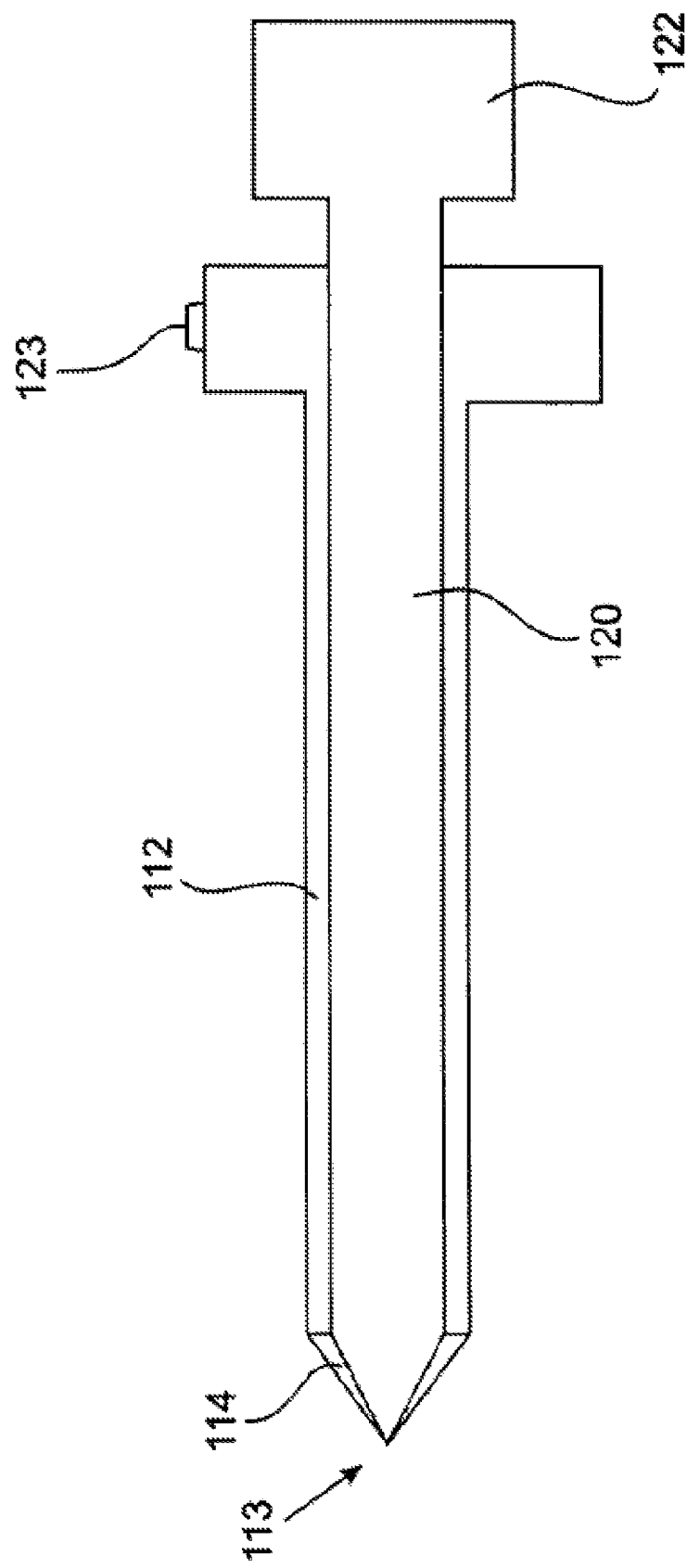
FIG. 15 is a sectional view of the system of FIG. 11, with an obturator received therein and the petals in a closed position.

In a second preferred embodiment, the present invention provides an expandable tip nerve surveillance cannula system 110 comprising an endoscopic hollow cannula shaft 112 having an expandable tip 113 comprised of a plurality of petals 114 (the details of petals 114 are better shown in FIGS. 12, 13, and 14). System 110 further comprises an obturator 120 which is slidably received within cannula shaft 112. As is shown in FIG. 15, obturator 120 is a rigid structure which provides internal support to cannula shaft 112 such that cannula shaft 112 can be received percutaneously. Shaft 112 can have a cross section which is circular, oval, racetrack-shaped or any other design. By holding obturator handle 122, the surgeon is able to advance cannula shaft 112 through the patient's para-spinal musculature and dock expandable tip 113 at the patient's annulus.

As seen in FIGS. 12 and 13, expandable tip 113 is comprised of a plurality of petals 114, held together by breakable seals 115. Breakable seals 115 can be formed by an elastomeric material with predictable failure segments between the petals. In one preferred aspect each of petals 114 has an electrode 116 disposed therein as shown. Electrodes 116 serve the following important functions.

Figure 16:
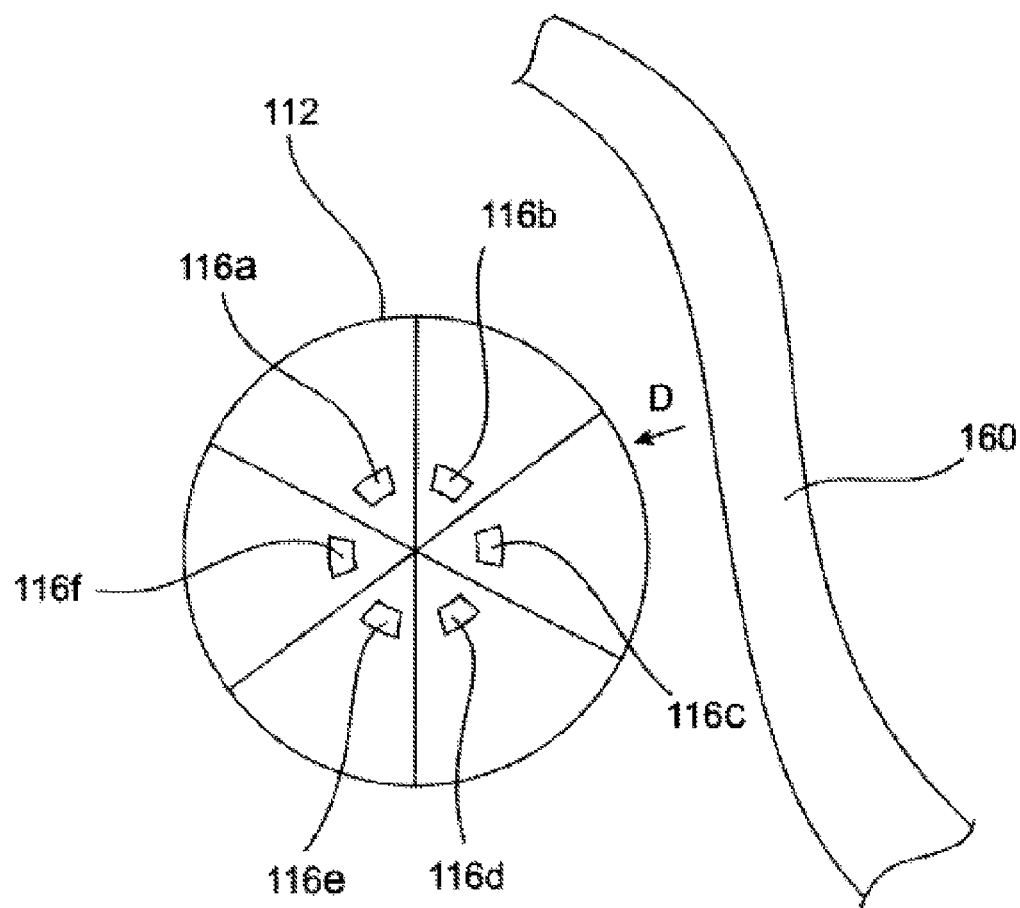
FIG. 16 is a schematic illustration of the electrodes at the distal tip of the present invention, the electrodes being used to sense the position of a para-spinal nerve.

First, electrodes 116 can be used for electromyography, and in particular to sense the presence and relative position of para-spinal nerves as cannula shaft 112 is advanced. Referring to FIG. 16, as can be seen electrodes 116a, 116b, 116c, 116d, 116e and 116f are disposed radially about cannula shaft 112, with one electrode disposed in each of petals 114, as has been described. Electrodes 116a, 116b, 116c, 116d, 116e and 116f assist in sensing the presence and location of para-spinal nerve 160 as follows. The electrodes closest to nerve 160 (in this case electrodes 116b and 116c, and to a lesser degree, electrodes 116a and 116d) will operate to depolarize nerve 160 such that the presence of nerve 160 can be detected by electromyography. As such, shaft 112 can be moved in direction D, thereby avoiding nerve 160 as shaft 112 is inserted. Alternatively, of course, shaft 112 can be moved in the opposite direction to D, such that cannula shaft 112 gently moves nerve 160 out of the way. Moreover, when none of electrodes 116a, 116b, 116c, 116d, 116e and 116f sufficiently stimulate to depolarize the nerve, and thereby assist in its detection, shaft 112 can be safely advanced toward the patient's intervertebral space. Should each one of electrodes 116a, 116b, 116c, 116d, 116e and 116f depolarize the nerve, this would indicate that the nerve is directly in front of the advancing cannula shaft 112. Accordingly, the cannula shaft could be moved such that contact with the nerve is avoided.

Alternatively, when none of electrodes 116a, 116b, 116c, 116d, 116e and 116f indicate the presence of a nerve, electrodes 116a, 116b, 116c, 116d, 116e and 116f can be powered to a higher level such that a cauterization of minor blood vessels can be achieved by passing increased electric current between each of the various adjacent electrodes, thus cauterizing adjacent blood vessels. Preferably, the present invention comprises a safety system such that cauterization power levels for electrodes 116 are not activated when any of electrodes 116 sense the presence of a para-spinal nerve thereby.

Preferably, each of electrodes 116a, 116b, 116c, 116d, 116e and 116f are operated in sequence, affording a sufficient latency period therebetween for the detection of an electromyographic signal.

Figure 11:
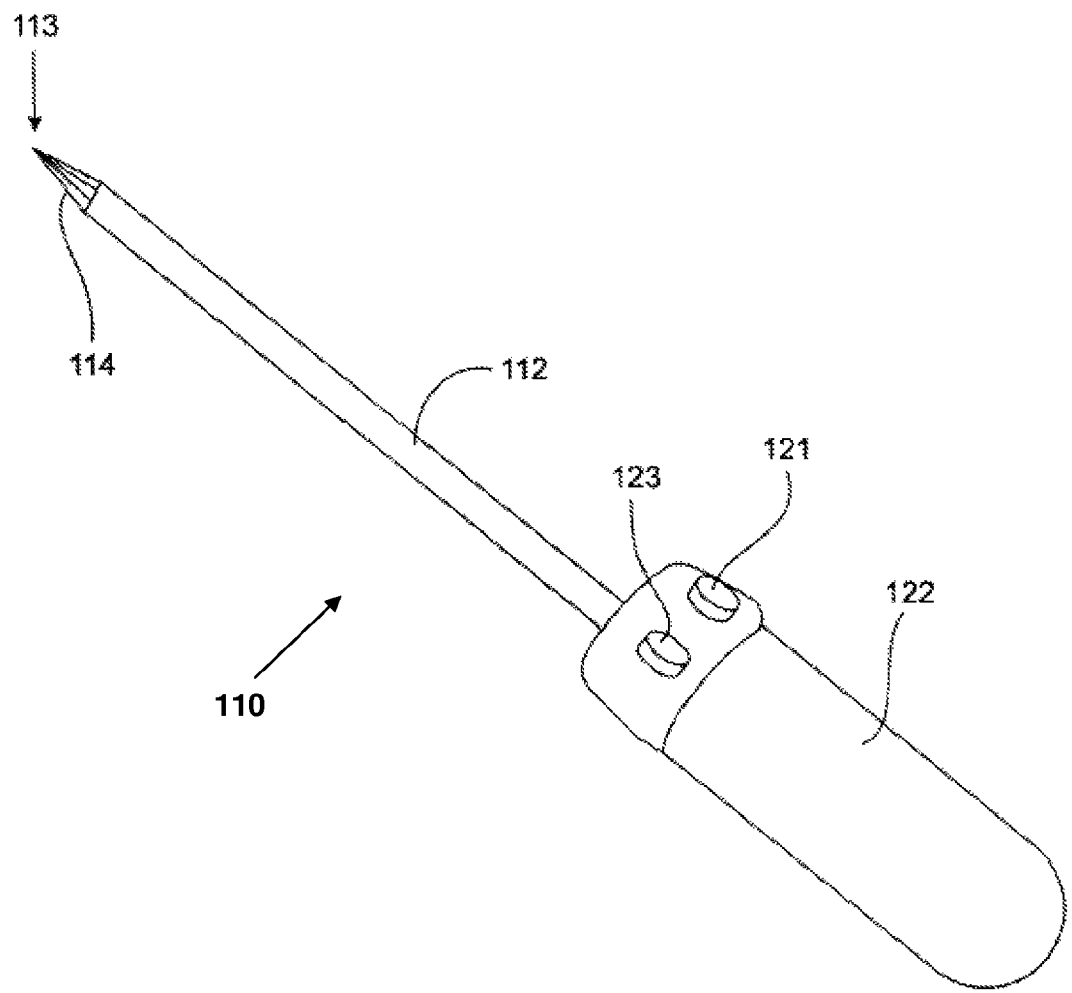
FIG. 11 is an illustration of an expandable tip nerve surveillance probe of the present invention.

As seen in FIG. 11, button 121 can be used to activate the blood vessel cauterization functions. Buttons 121 and 123 are conveniently located on the near handle 122 such that they may be activated while the surgeon grips obturator handle 122.

Figure 17:
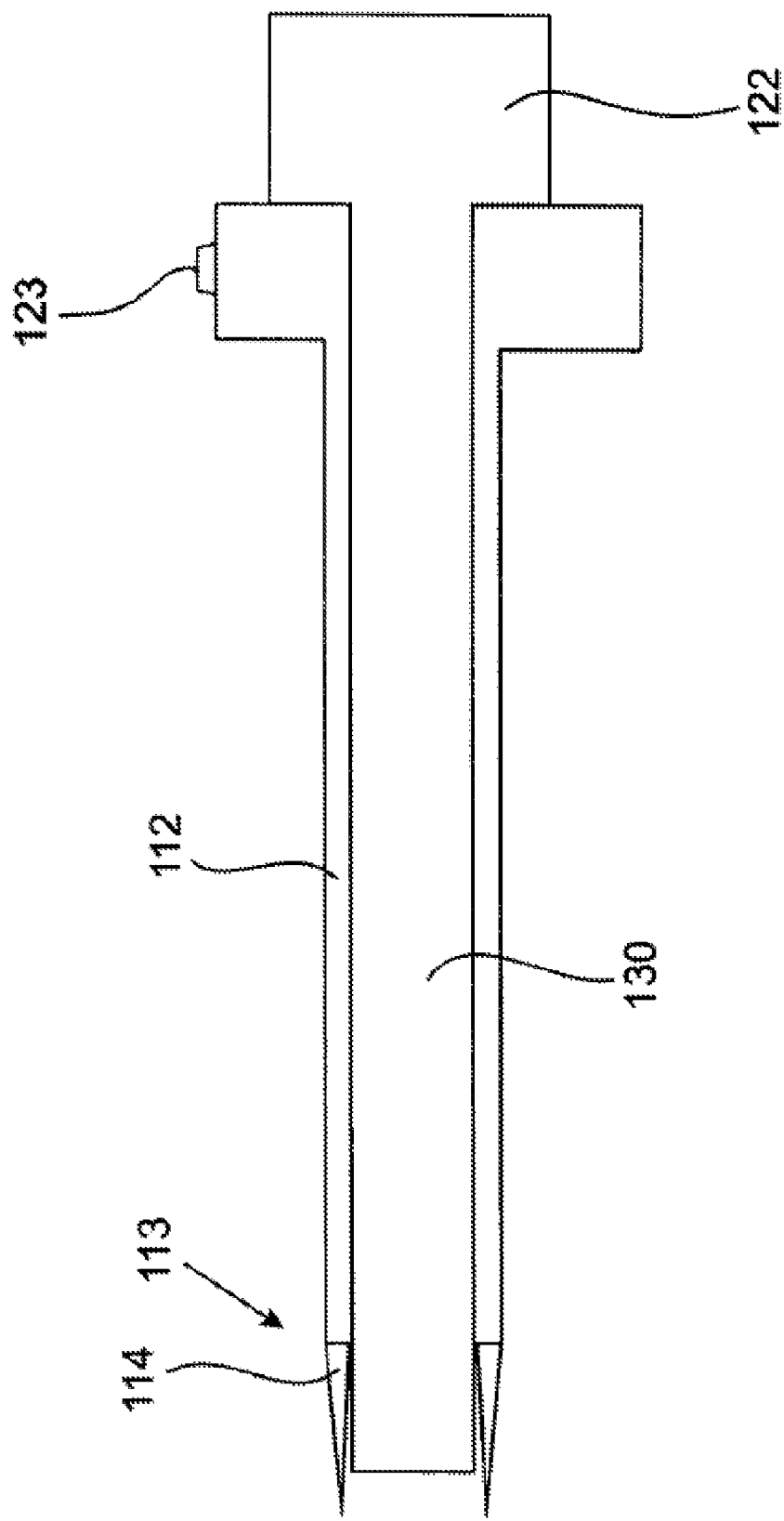
FIG. 17 is a sectional view of the system of FIG. 11 with an inner cannula received therein and the petals in an open position.

Subsequent to being positioned at the patient's annulus, obturator 120 is removed from cannula shaft 112. As seen in FIG. 17, inner cannula 130 is then inserted into cannula shaft 112. Inner cannula 130 is then inserted into cannula shaft 112. Inner cannula 130 is dimensioned to be of a size that, when fully inserted into shaft 112, inner cannula 130 breaks apart seals 115, forcing petals 114 to be displaced radially outwards to a distance of at least the internal diameter of shaft 112 as shown. Inner cannula 130 can alternately comprise a solid rod or obturator which is dimensioned to be received within shaft 112 to open petals 114.

As can be seen in FIG. 13, a notch 118 is found between adjacent petals 114 where petals 114 are mounted to the distal end 113 of cannula shaft 112. Notches 118 operate to facilitate breakage of seals 115 by providing a stress relief region at the base of breakable seals 115.

Figure 18:
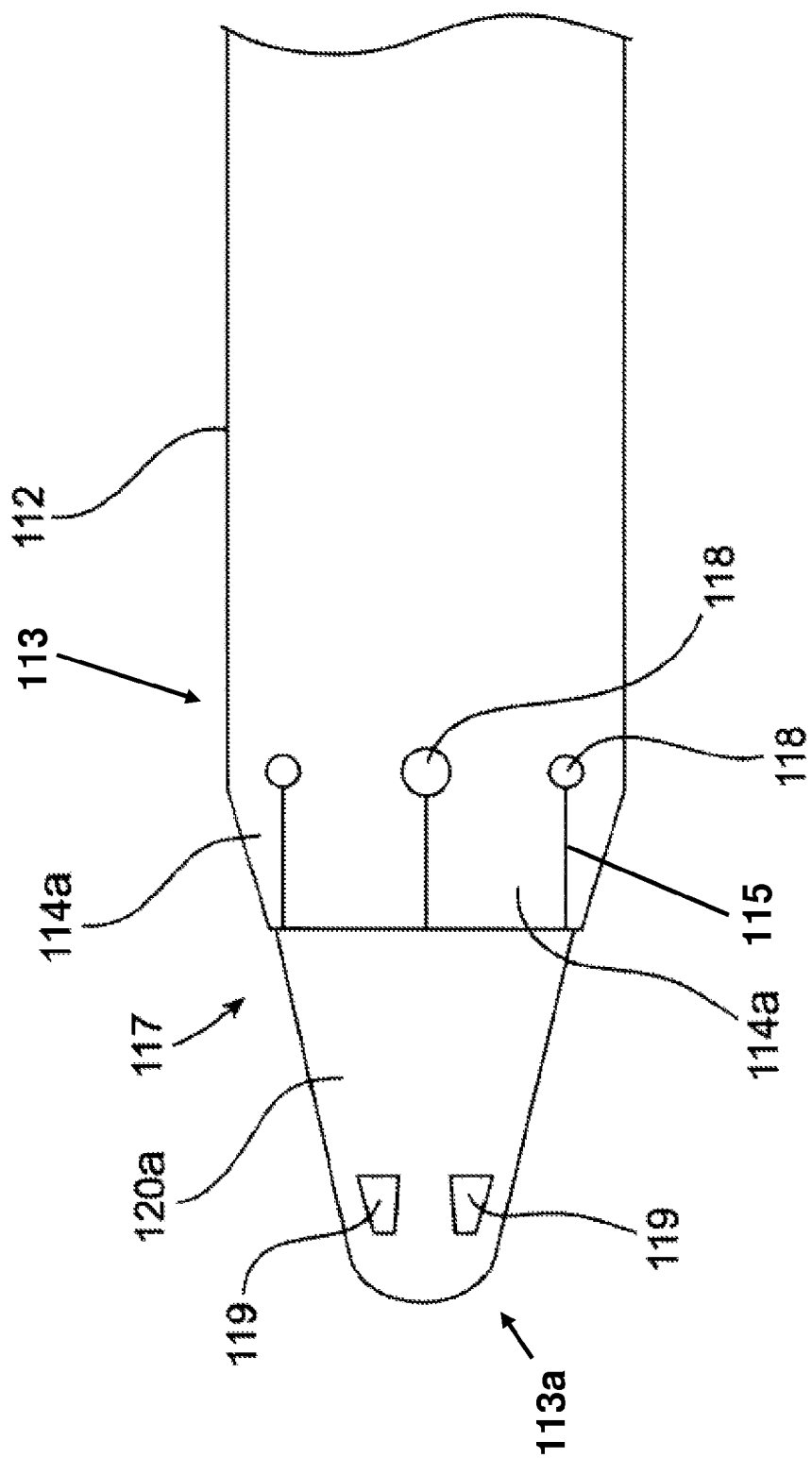
FIG. 18 is a side view of an alternate embodiment of the distal tip region of the present invention having truncated petals.
Figure 19:
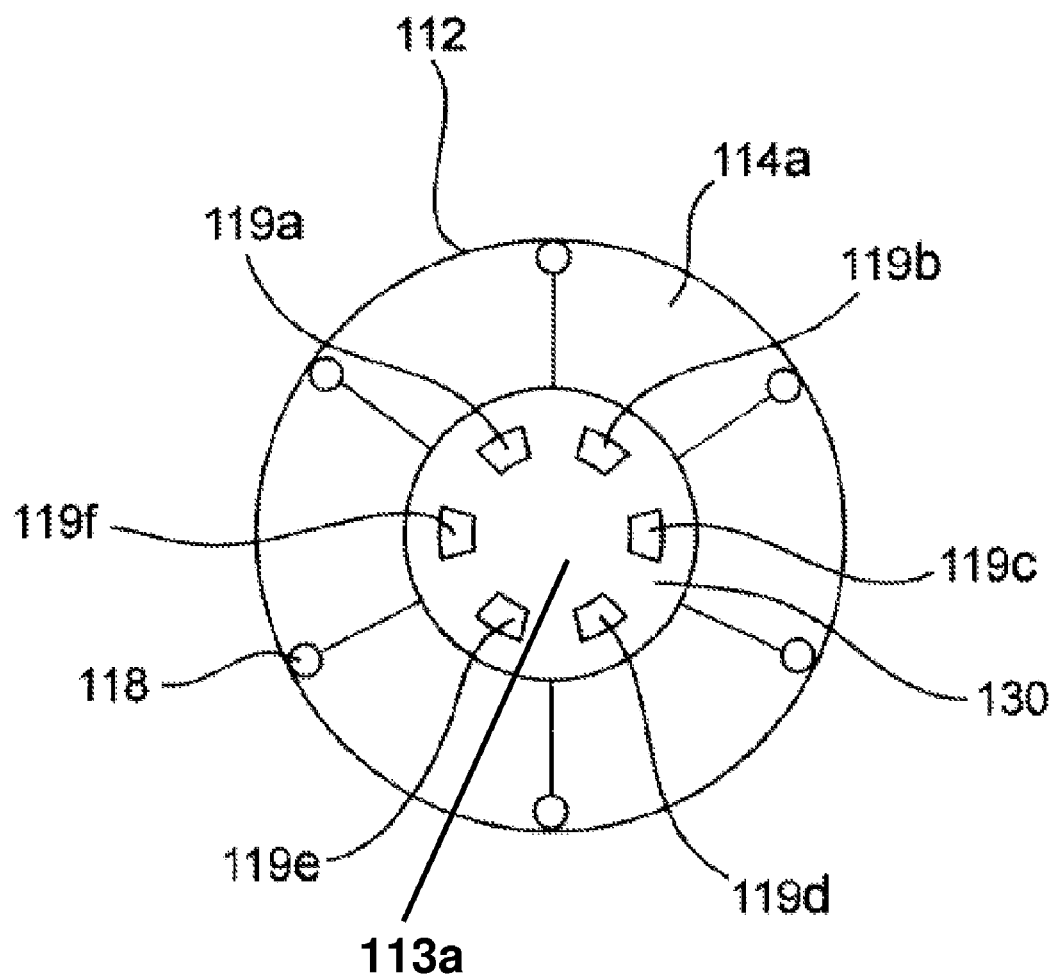
FIG. 19 is an end view corresponding to FIG. 18.

In an alternate design, as shown in FIGS. 18 and 19, distal tip 113 comprises truncated petals 114a which, when sealed together by way of breakable seals 115, meet at their distal end to define a small opening 117 at distal tip 113 of cannula shaft 112. In this design, an obturator 120a is slidably received within cannula shaft 112. Obturator 120a has a narrow distal end 113a which protrudes through opening 117. Electrodes 119a, 119b, 119c, 119d, 119e and 119f are disposed radially about the narrow distal end 113a of obturator 120a, functioning similar to the probe design shown in FIG. 6.

In this alternate design of FIGS. 18 and 19, nerve surveillance and blood vessel cauterization functions as described above and as performed by electrodes 116 on petals 114 are instead performed by electrodes 119 on obturator 120a. In this aspect of the invention, petals 114a are truncated and obturator 120a protrudes therethrough.

Figure 20:
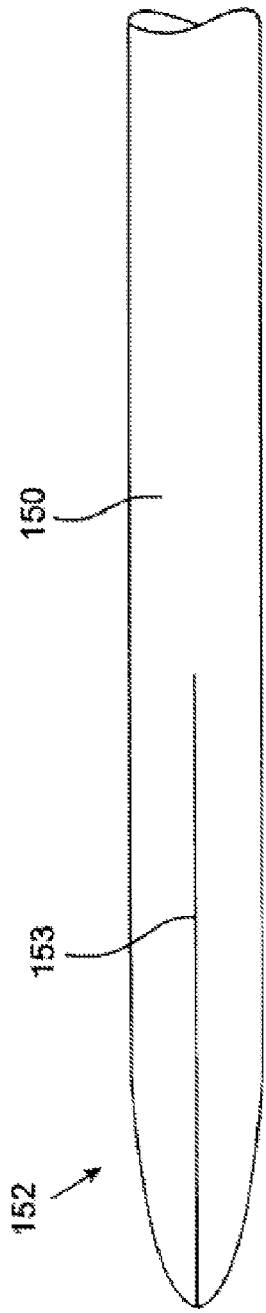
FIG. 20 is a top plan view of a peel back expandable tip cannula.
Figure 21:
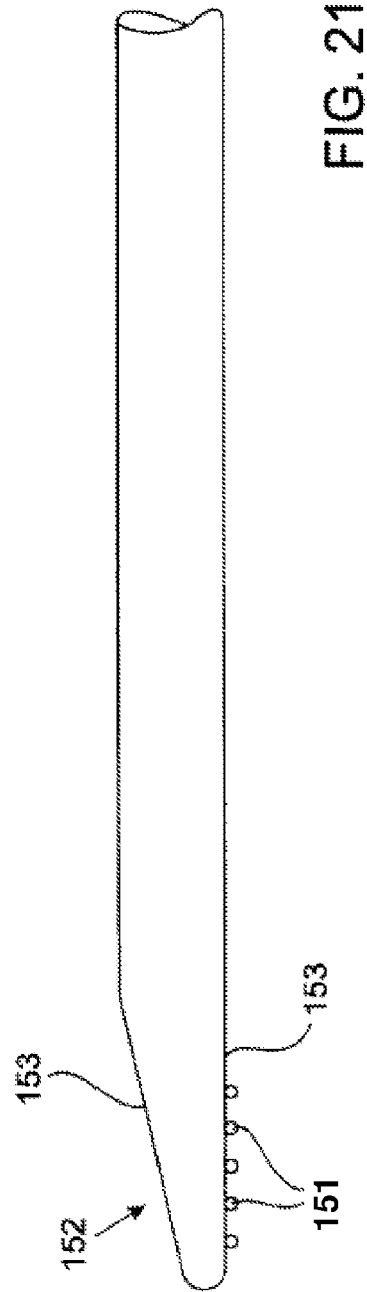
FIG. 21 is a side elevation view of the peel back cannula FIG. 20.

In another alternate embodiment, a peel back cannula having an expandable tip is provided. Referring to FIG. 20, cannula 150 is provided. Cannula 150 has a tapered narrow distal end 152 and a tear away line 153 which is formed in the preferred polymeric material of cannula 150. Tear away line 153 will split under tension as will be explained. Cannula 150 may also comprise electrodes 151 which perform a similar function to the electrodes 116 described herein. Electrodes 151 can be disposed axially along the length of cannula 150, or radially around the distal end of cannula 150, or some combination thereof.

An advantage of being disposed axially along the cannula is that electrodes 151 will be able to sense the position of a nerve relative to the cannula in an axial dimension. Similarly, an advantage of being disposed radially around the cannula is that the electrodes will be able to sense the position of a nerve relative to the cannula in a radial dimension. It is to be understood that all embodiments of the present invention comprise the concept of nerve surveillance electrodes disposed both radially around and axially along the nerve surveillance cannula or obturator, and that the radial electrode placement shown in the design of FIGS. 7, 8 and 11 to 19, and the axial electrode placement shown in the design of FIGS. 20 to 23 is not limiting.

In a preferred method of operation, cannula 150 is advanced such that its tapered end 152 is adjacent nerve 160 as is seen in FIG. 22. An obturator 155 is positioned within cannula 150. Obturator 155 provides structural support for the cannula as it is being inserted or as it is moving a nerve. Obturator 155 provides structural support for the cannula as it is being inserted or as it is moving a nerve. Obturator 155 is thereafter removable such that cannula 150 operates as an open passageway as will be explained.

Figure 24:
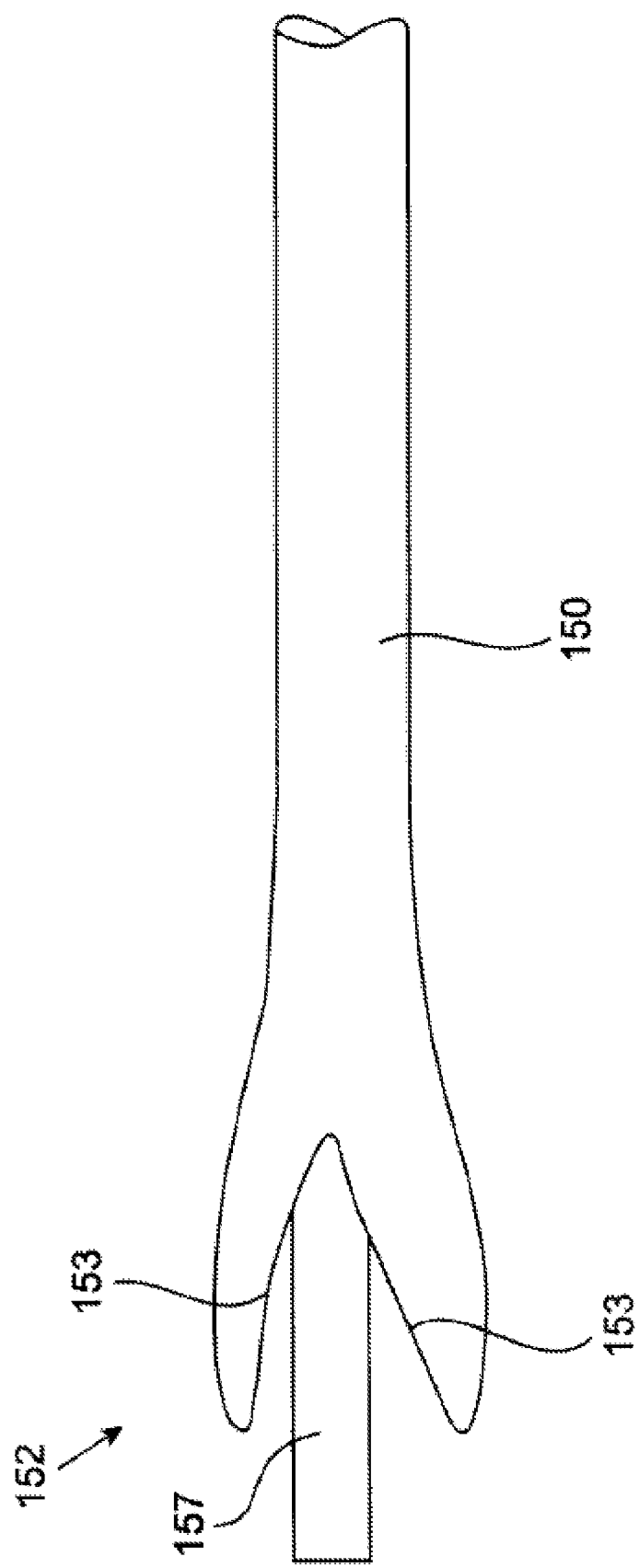
FIG. 24 is a top plan view corresponding to FIG. 23.

A narrow inner cannula 157 may also be provided. Cannula 157 is received around obturator 155 and within cannula 150. When the operator has determined it is safe and desirable to open cannula 150, inner cannula 157 is advanced to the position shown in FIGS. 23 and 24. Specifically, inner cannula 157 pushes against the tapered end 152 of cannula 150 causing cannula 150 to split open along tear away line 153. Accordingly, inner cannula 157 can be used to provide a cannulated passageway when obturator 157 has been withdrawn therefrom. Alternatively, inner cannula 157 can be replaced by suitably dimensioned obturator for opening cannula 150 along tear away line 153.

Tear away line 153 may be formed by scribing the polymeric material forming cannula 150. Tear away line 153 preferably runs some distance along opposite sides of the open end 152 of cannula 150. Alternatively, tear away line 153 can be disposed along the top and bottom of cannula 150 as shown.

Figure 25:
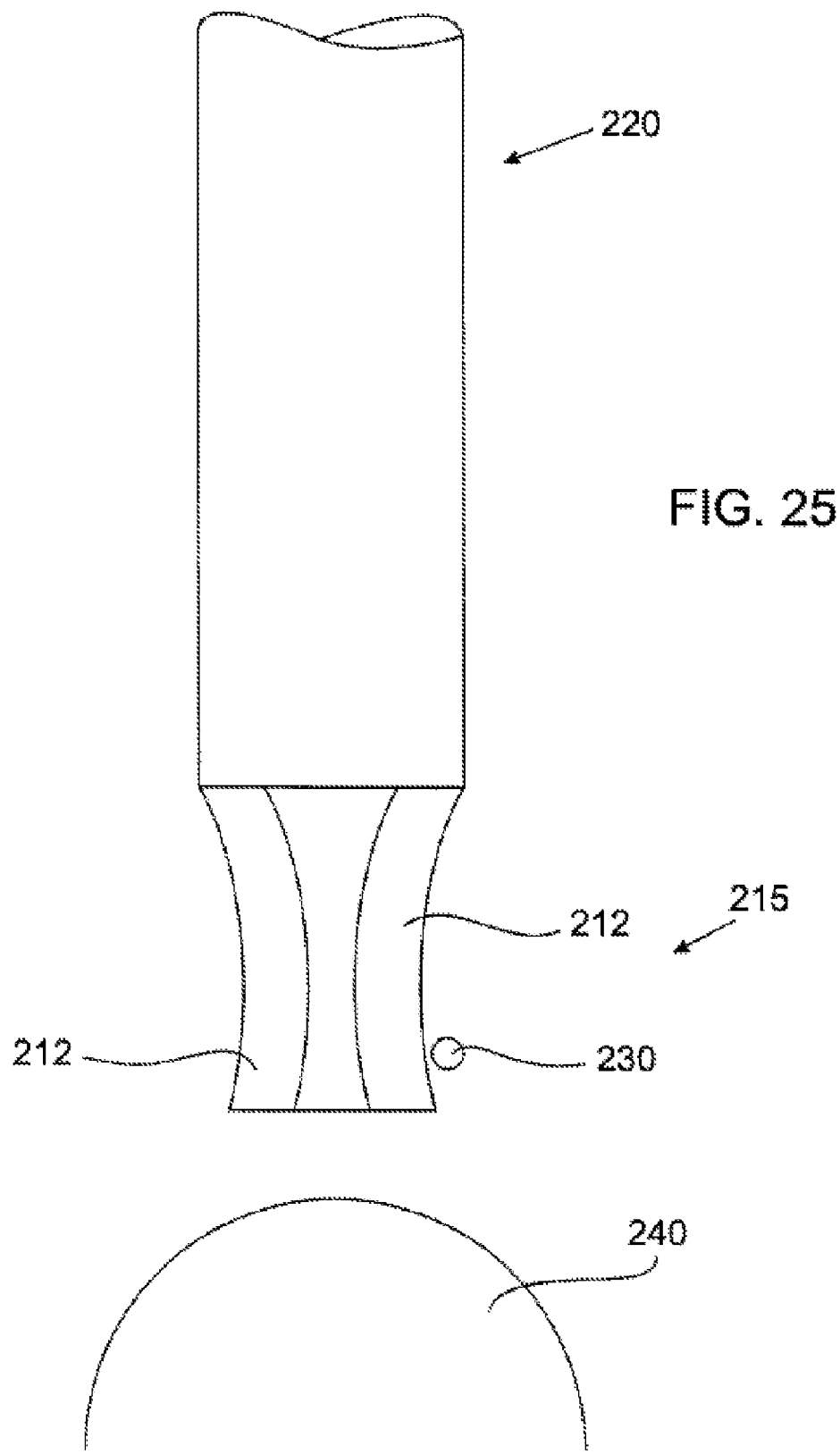
FIG. 25 is a side elevation view of a curved petal nerve surveillance probe.
Figure 26:
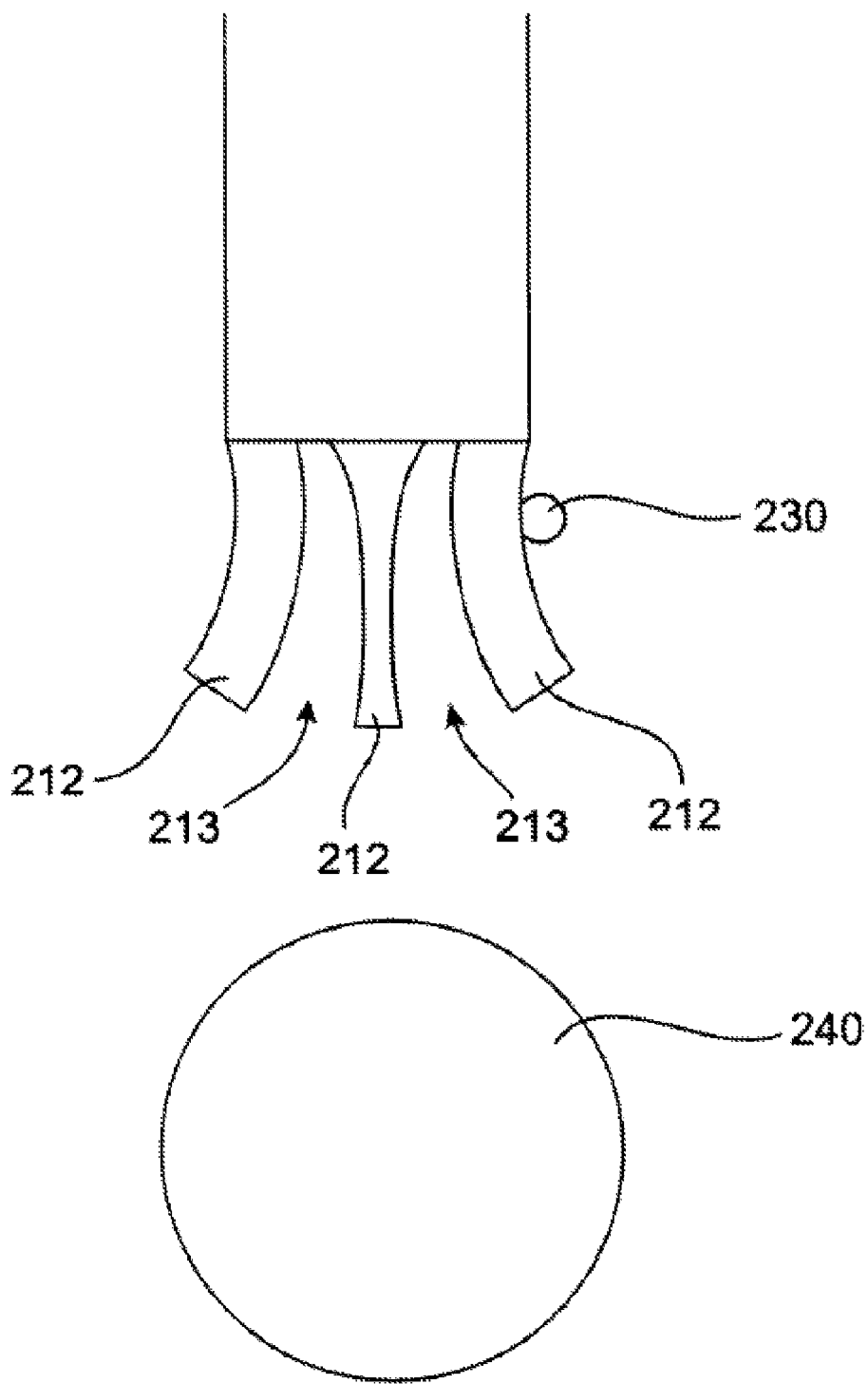
FIG. 26 is a side elevation view corresponding to FIG. 25, but with the petals in an open position.

FIG. 25 is a side view of a curved petal design of the present invention in a closed position with cannula 220 having outwardly curved petals 212 at distal end 215. A nerve 230 is disposed adjacent the ends of closed petals 212 as shown. Petals 212 are then opened, using methods described herein, as shown in FIG. 26. The opening of petals 212 causes nerve 230 to be generally displaced upward away from an operative site which may preferably comprise a patient's intervertebral disk 240.

Figure 27:
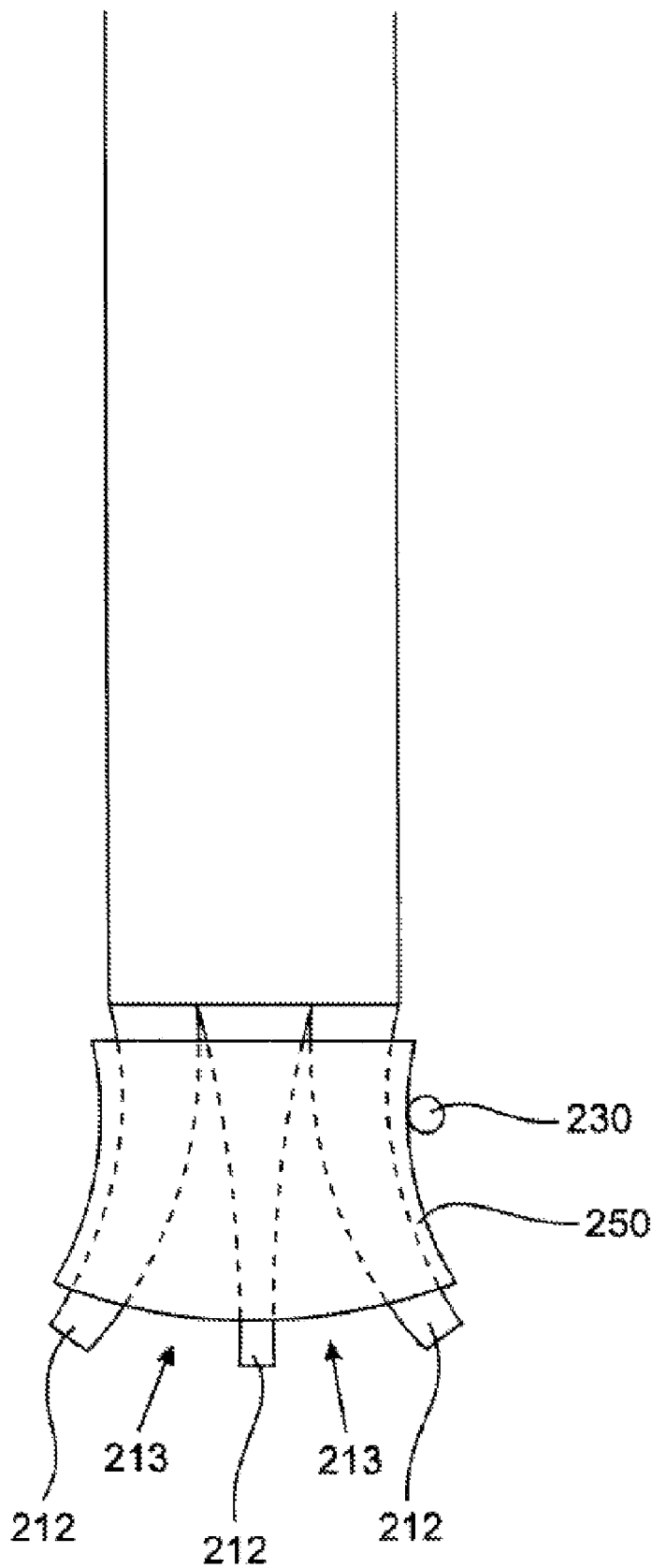
FIG. 27 is a view corresponding to FIG. 26, but with an expandable elastomer shown wrapped around the distal end of the curved petals.

As shown in FIG. 27, an elastomer 250 can be wrapped around the petals 212 such that nerves are not pinched in gaps 213 between the adjacent petals either when the petals are first opened or when the petals are closed during the removal of the cannula from the patient. It is to be appreciated that elastomer 250 could also be wrapped around the ends of any of the straight petal designs shown in FIGS. 11 to 19.

The operative site or target site may comprise a patient's intervertebral disk 240 when the present invention is used in minimally invasive spinal surgery. It is to be understood, however, that the present expandable tip cannula can be used in all manner of minimally invasive surgery and is especially useful for approaching any target site having sensitive nerves adjacent thereto since the present invention is specifically adapted to gently push the nerve out of the way as the petals are opened, thereby providing a cannulated access portal for the insertion and removal of various surgical devices through cannula 220.

Figure 28:
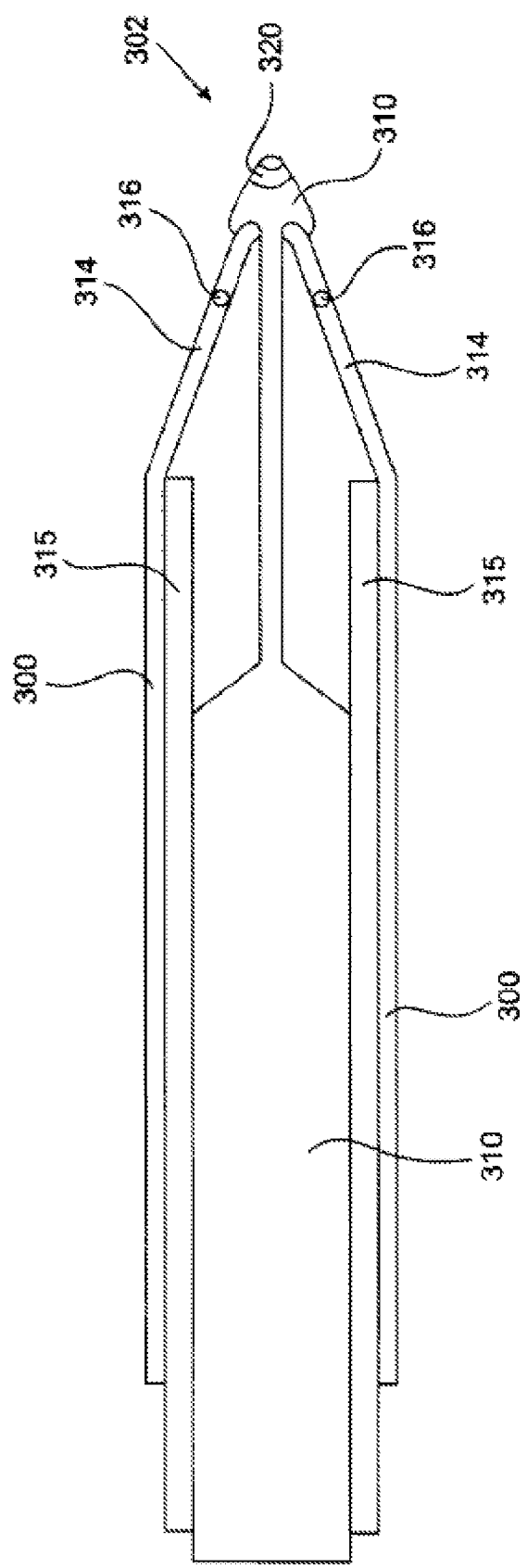
FIG. 28 is a sectional elevation view of the distal end of an alternate nerve surveillance cannula.

FIG. 28 shows an alternate design of the distal end 302 of a nerve surveillance cannula 300. Cannula 300 has a plurality of expanding petals 314, with each petal 314 comprising an electrode 316 adapted for nerve surveillance or blood vessel cauterization as described above. In this aspect of the invention, an obturator 310 protrudes through an opening between petals 314, as shown. As can be seen, obturator 310 may preferably be tapered to a narrow distal end 302, which assists in easing cannula 300 through the patient's facia and paraspinal musculature and into the patient's intervertebral space. In addition, distal end 302 of obturator 310 can be shaped to latch against the ends of petals 314, as shown, thereby assisting in holding together petals 314 as cannula 300 is advanced.

Preferably, obturator 310 further comprises a centrally disposed electrode 320. Electrode 320, being axially displaced from electrodes 316 is adapted to sense the position of a nerve in the axial direction as probe 300 approaches the nerve. Subsequent to placement at the patient's intervertebral space, an internal cannula 315 can be advanced distally to open petals 314 with obturator 310 being advanced slightly to first un-latch the distal ends of petals 314 and then withdrawn from cannula 300, providing a cannulated access to the patient's intervertebral space.

Figure 29:
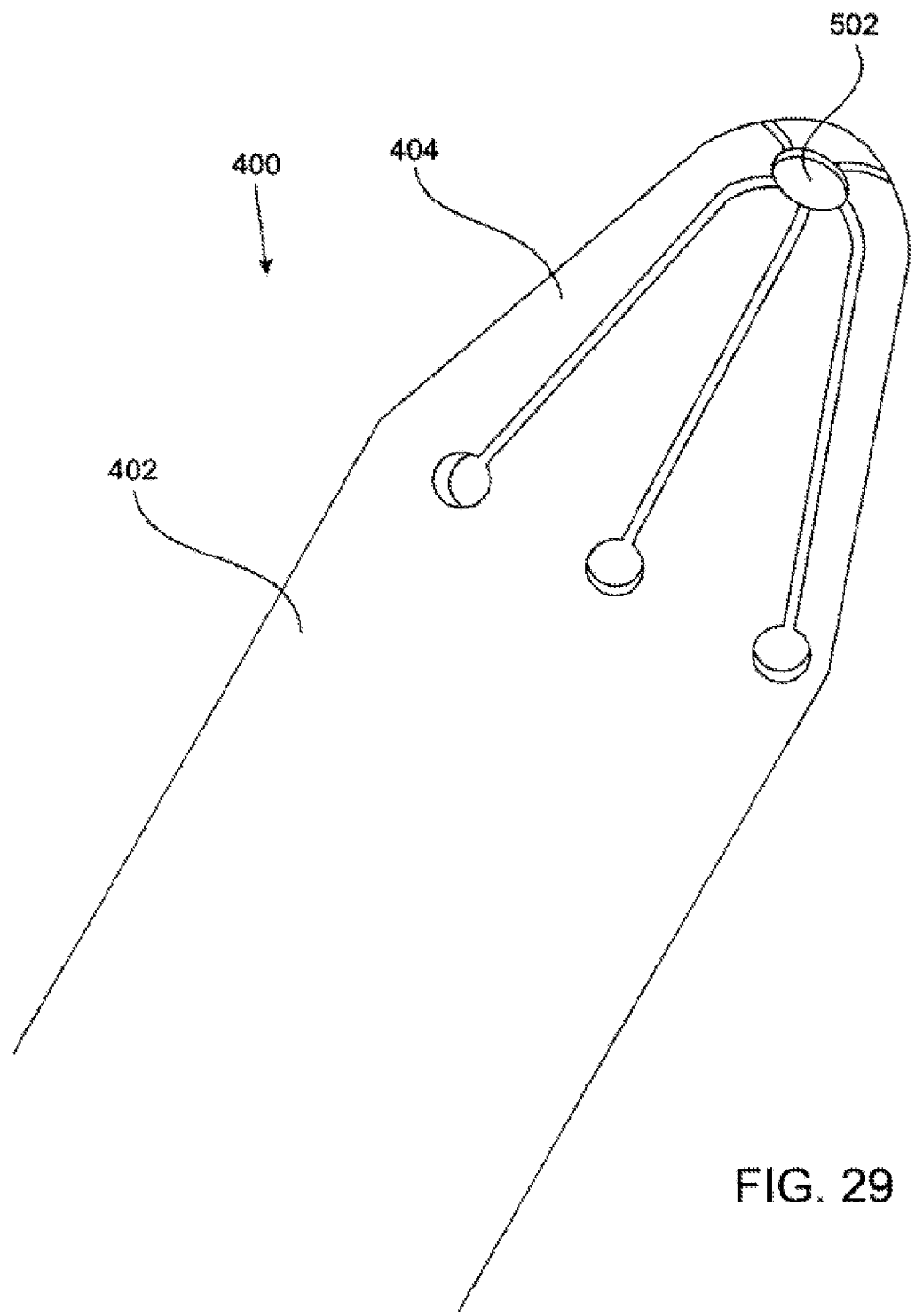
FIG. 29 is a perspective view of an alternate nerve surveillance probe.
Figure 30:
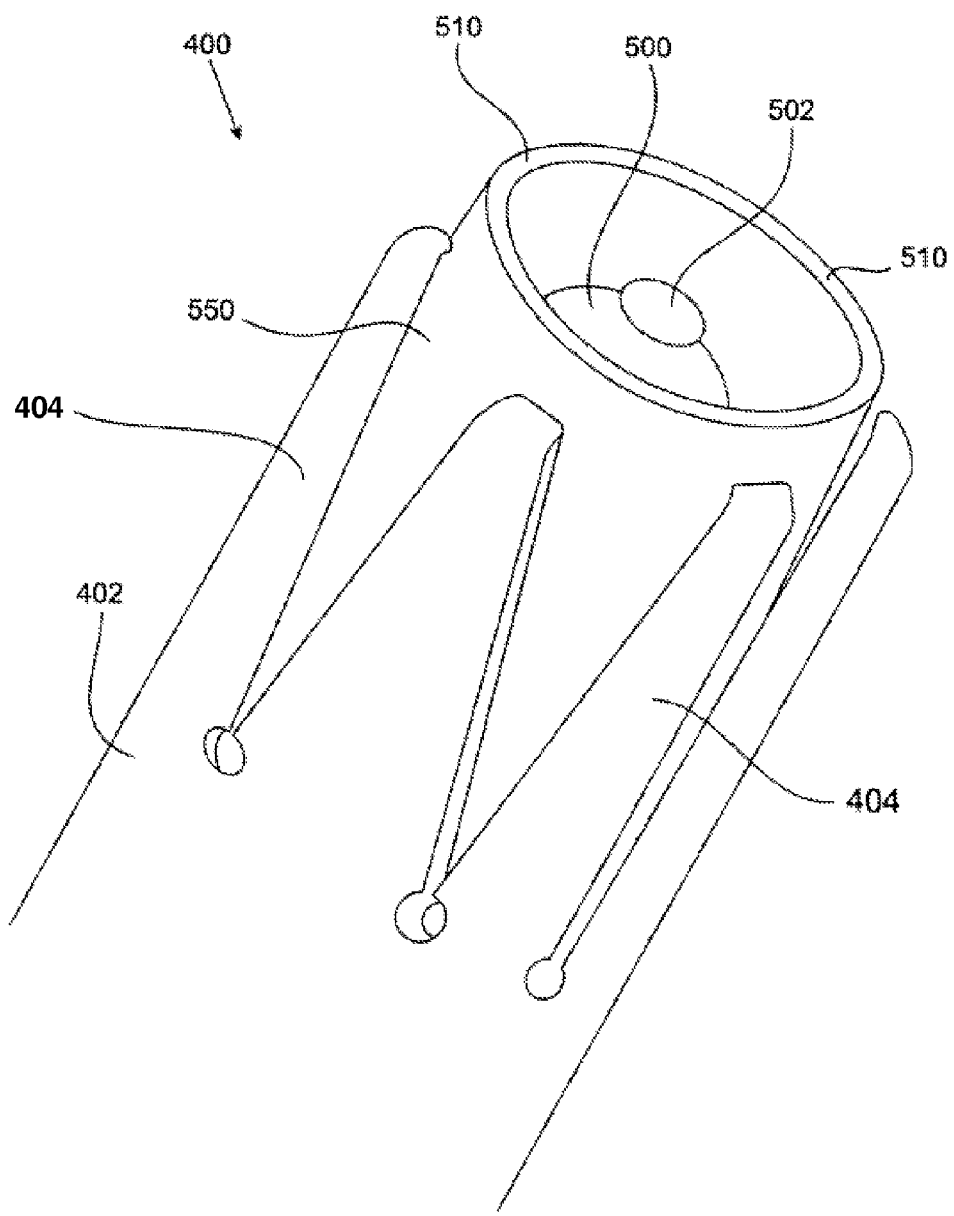
FIG. 30 shows the surveillance probe of FIG. 29 with the petals opened by an inner cannula.

FIG. 29 through 33 show an alternative nerve surveillance cannula and probe system 400, comprising a cannula 402 having a plurality of radially outwardly extending petals 404. An internal obturator 500 is received within cannula 402. Obturator 500 has an electrode 502 disposed at its distal end as shown in FIG. 30. Electrode 502 can also be seen at distal end of cannula 402 in FIG. 29. Electrode 502 operates to stimulate and thereby, depolarize a nerve as cannula 402 is advanced towards the patient's intervertebral space. FIG. 29 shows cannula 402 with petals 404 closed around electrode 502 as the cannula is advanced.

Figure 31:
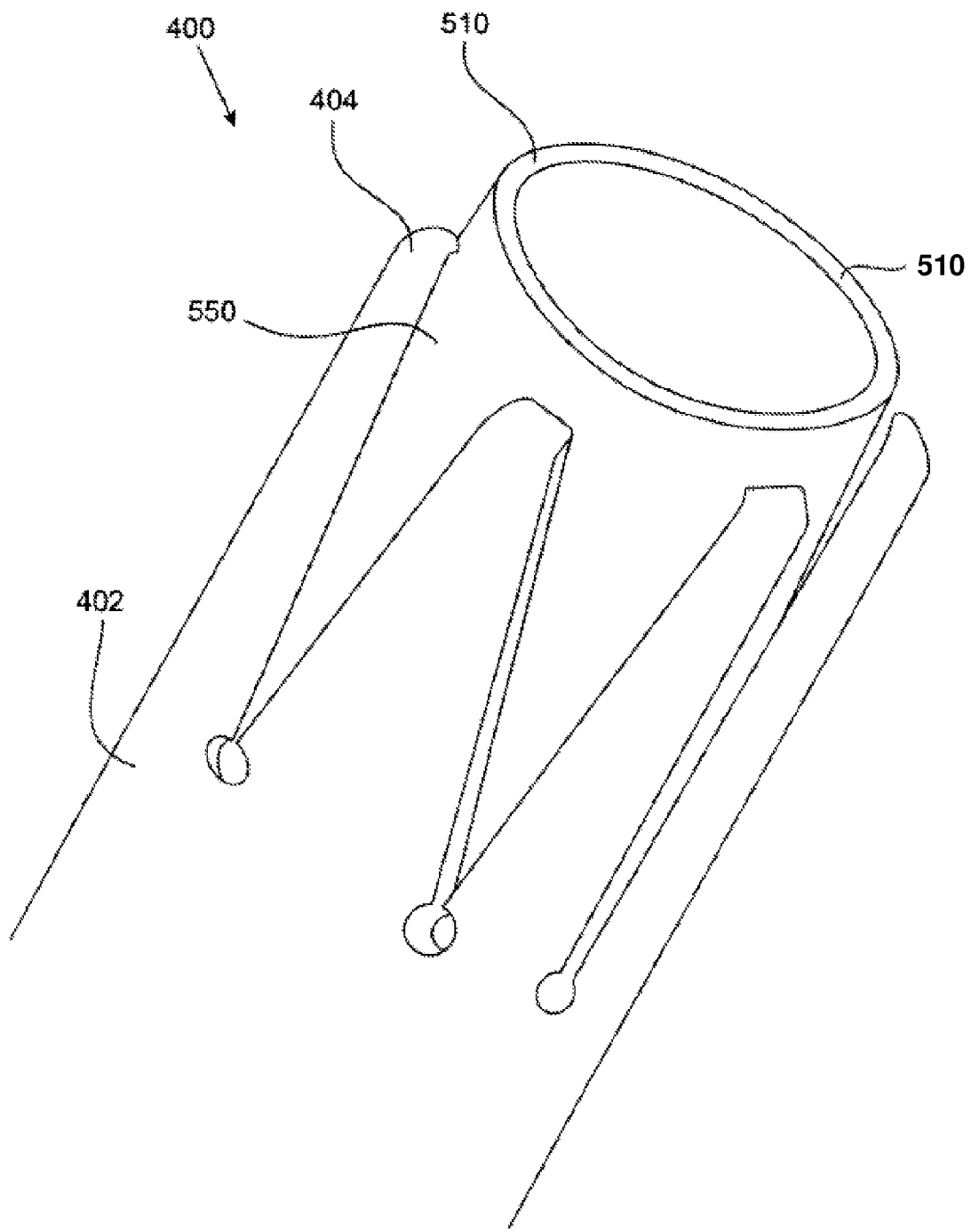
FIG. 31 corresponds to FIG. 30, but with the internal obturator removed.

FIG. 30 shows an inner cannula 550 which is advanced through cannula 402 to open petals 404 as shown. Inner cannula 550 preferably comprises an electrode 510 which is disposed around the distal end of the cannula, as shown. After inner cannula 550 has opened petals 404, as shown, electrode 502 is turned off and obturator 500 is removed from inner cannula 550 as is shown in FIG. 31. Electrode 510 remains turned on such that it is adapted to detect whether a nerve is positioned close to entering within cannula 550, or whether a surgical instrument advanced through cannula 550 would contact a nerve proximal electrode 510.

Figure 32:
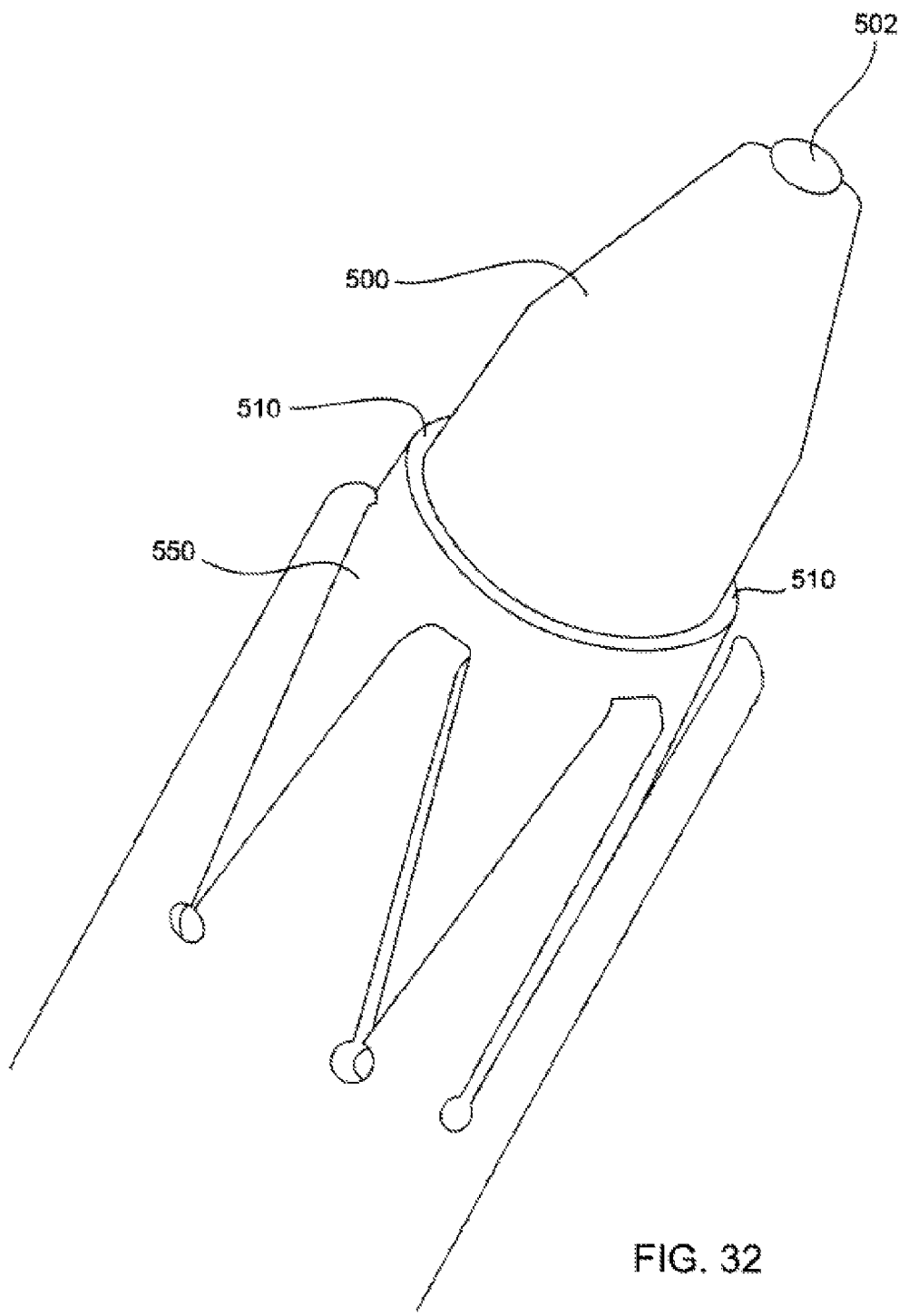
FIG. 32 corresponds to FIG. 30, but with the internal obturator advanced distally.

As is shown in FIG. 32, obturator 500 can thereafter be advanced through cannula 550 to bluntly divide and dilate the annulus of a disc. In this aspect of the invention, electrode 502 is turned off as the annulus is divided and dilated. Annular electrode 510 may preferably be turned on during this procedure to sense the presence of nerves adjacent the distal end of cannula 550.

Figure 33:
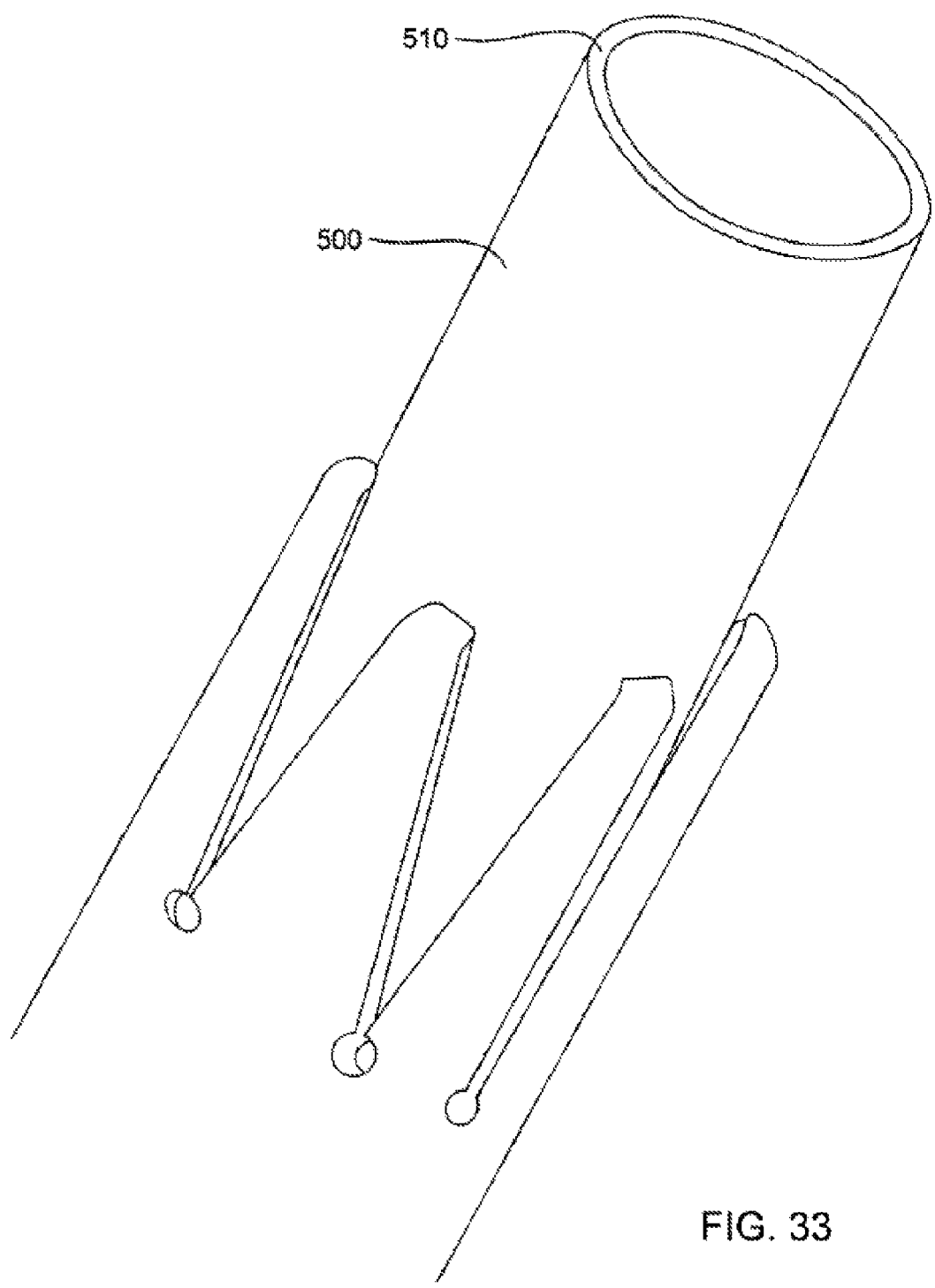
FIG. 33 corresponds to FIG. 31, but with the internal cannula advanced distally.

As is seen in FIG. 33, after the annulus has been divided and dilated, obturator 500 can be withdrawn from cannula 550 with cannula 550 advanced distally into the hole cut into the annulus. As such, a safe cannulated access way into the annulus or other region of the patient's body is provided.

What is claimed is:

1. A method of performing spine surgery, comprising:
   minimally invasively advancing a nerve surveillance instrument and a surgical access instrument towards a spinal target site, wherein the nerve surveillance instrument is dimensioned to be slidably received within the surgical access instrument and the surgical access instrument defines a passageway through which an implant can be passed for introduction into said spinal target site, the nerve surveillance instrument having at least one nerve stimulation electrode disposed proximate a distal end thereof;
   energizing at least one nerve stimulation electrode disposed proximate a distal end of the nerve surveillance instrument while advancing the nerve surveillance instrument towards the surgical target site to detect the presence of nerves adjacent said nerve surveillance instrument;
   removing said nerve surveillance instrument from said passageway after said surgical access instrument has been advanced to said spinal target site;
   separating tissue displacement members of said surgical access instrument; and
   introducing said implant into said spinal target site through said separated tissue displacement members.

2. The method of claim 1, wherein said at least one nerve stimulation electrode comprises a plurality of nerve stimulation electrodes and wherein the step of advancing comprises the further sub-step of sensing the presence of said nerves in a radial direction relative to a central axis of said surgical access instrument through the use of the plurality of nerve stimulation electrodes which are radially disposed around said distal end of said nerve surveillance instrument.

3. The method of claim 1, wherein said step of introducing said implant includes using at least one of a bone decorticator, a camera, an articulating forcep and an intervertebral positioning system.

4. The method of claim 1, wherein said tissue displacement members comprise a plurality of petals, each of said plurality of petals having at least one nerve stimulation electrode disposed therein.

5. The method of claim 1, wherein said tissue displacement members are expandable from a first position to a second position.

6. The method of claim 5, wherein said tissue displacement members are provided in said first position and held together by breakable seals.

7. The method of claim 1, wherein said surgical access instrument is a cannula.

8. A method of performing spine surgery, comprising:
   minimally invasively advancing a nerve surveillance instrument and a surgical access instrument towards a spinal target site, wherein the nerve surveillance instrument is dimensioned to be slidably received within the surgical access instrument;
   delivering energy through at least one nerve stimulation electrode located proximate a distal end of said nerve surveillance instrument while advancing said nerve surveillance instrument and detecting electromyographic activity evoked by said delivered energy to detect the presence of nerves adjacent said nerve surveillance instrument;
   removing said nerve surveillance instrument from said surgical access instrument after said surgical access instrument has been advanced to said spinal target site;
   opening said surgical access instrument to create a passageway configured to pass an implant into said spinal target site; and
   introducing an implant through said passageway and into said spinal target site.

9. The method of claim 8, wherein said step of opening said surgical access instrument involves moving a first portion of said surgical access instrument away from a second portion of said surgical access instrument.

10. The method of claim 9, wherein a distal end of said surgical access instrument comprises a plurality of tissue displacement members, each of said plurality of tissue displacement members having at least one nerve stimulation electrode disposed therein, said tissue displacement members being movable from a first position to a second position.

11. The method of claim 10, wherein said tissue displacement members are provided in said first position and held together by breakable seals.

12. The method of claim 8, wherein said surgical access instrument is a cannula.

\* \* \* \* \*